United States Patent
Jarosz et al.

(10) Patent No.: US 10,287,623 B2
(45) Date of Patent: May 14, 2019

(54) METHODS AND COMPOSITIONS FOR TARGETED NUCLEIC ACID SEQUENCING

(71) Applicant: 10X Genomics, Inc., Pleasanton, CA (US)

(72) Inventors: Mirna Jarosz, Mountain View, CA (US); Michael Schnall-Levin, Palo Alto, CA (US); Serge Saxonov, Oakland, CA (US); Benjamin Hindson, Pleasanton, CA (US); Xinying Zheng, Mountain View, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 15/174,928

(22) Filed: Jun. 6, 2016

(65) Prior Publication Data
US 2016/0281138 A1 Sep. 29, 2016

Related U.S. Application Data

(63) Continuation of application No. 14/927,297, filed on Oct. 29, 2015.

(60) Provisional application No. 62/072,164, filed on Oct. 29, 2014.

(51) Int. Cl.
| | | |
|---|---|---|
| *C12Q 1/68* | (2018.01) | |
| *C12Q 1/6806* | (2018.01) | |
| *C12Q 1/6874* | (2018.01) | |
| *C12Q 1/6837* | (2018.01) | |
| *C07H 21/02* | (2006.01) | |

(52) U.S. Cl.
CPC ......... *C12Q 1/6806* (2013.01); *C12Q 1/6837* (2013.01); *C12Q 1/6874* (2013.01)

(58) Field of Classification Search
CPC ........ C12Q 2535/122; C12Q 2537/159; C12Q 2565/514; C12Q 1/6806; C12Q 1/6874; C12Q 2563/179; C12Q 1/6837
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Gerald |
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kozak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,900,481 A | 5/1999 | Lough et al. |
| 5,958,703 A | 9/1999 | Dower et al. |
| 5,965,443 A | 10/1999 | Reznikoff et al. |
| 5,994,056 A | 11/1999 | Higuchi et al. |
| 5,997,636 A | 12/1999 | Gamarnik et al. |
| 6,033,880 A | 3/2000 | Haff et al. |

(Continued)

FOREIGN PATENT DOCUMENTS

| | | |
|---|---|---|
| EP | 0249007 A2 | 12/1987 |
| EP | 0271281 A2 | 6/1988 |

(Continued)

OTHER PUBLICATIONS

Amini et al. (on line publication date Oct. 19, 2014) Nature Genetics vol. 46 No. 12 pp. 1343-1349 doi:10.1038/ng.3119.*
Bodi et al. (Jul. 2013) J of biomolecular Techniques. 24:73-86.*
Kaper, F. et al., PNAS, vol. 110, pp. 5552-5557 (Apr. 2013).*
Kaper, F. et al., PNAS, vol. 110, (Apr. 2013) Supplemental data, pp. 1-7.*
Wesolowska, A. et al., Leukemia, vol. 25, pp. 1001-1006 (2011).*
U.S. Appl. No. 13/966,150, filed Aug. 13, 2013.
U.S. Appl. No. 14/175,935, filed Feb. 7, 2014.
U.S. Appl. No. 14/175,973, filed Feb. 7, 2014.
U.S. Appl. No. 14/316,383, filed Jun. 26, 2014.
U.S. Appl. No. 14/316,398, filed Jun. 26, 2014.
U.S. Appl. No. 14/316,416, filed Jun. 26, 2014.
U.S. Appl. No. 14/316,431, filed Jun. 26, 2014.

(Continued)

*Primary Examiner* — Teresa E Strzelecka
(74) *Attorney, Agent, or Firm* — Morgan, Lewis & Bockius LLP

(57) ABSTRACT

The present invention is directed to methods, compositions and systems for capturing and analyzing sequence information contained in targeted regions of a genome. Such targeted regions may include exomes, partial exomes, introns, combinations of exonic and intronic regions, genes, panels of genes, and any other subsets of a whole genome that may be of interest.

18 Claims, 8 Drawing Sheets

(56) References Cited

U.S. PATENT DOCUMENTS

| | | |
|---|---|---|
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong et al. |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,986,286 B2 | 3/2015 | Stone et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |

(56) References Cited

U.S. PATENT DOCUMENTS

| | | |
|---|---|---|
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,041,116 B2 | 8/2018 | Hindson et al. |
| 10,053,723 B2 | 8/2018 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jesperson et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Anh et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castilllo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtz et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |

(56) References Cited

U.S. PATENT DOCUMENTS

| | | |
|---|---|---|
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Gan-ell et al. |
| 2012/0003657 A1 | 1/2012 | Myllykangas et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0295819 A1 | 11/2012 | Leamon et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1* | 5/2013 | Chen .................. C12Q 1/6874 506/2 |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | DeSimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0093916 A1 | 4/2014 | Belyaev |
| 2014/0120529 A1 | 5/2014 | Andersen et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarssib et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0304860 A1 | 10/2016 | Hindson et al. |

(56) References Cited

U.S. PATENT DOCUMENTS

| | | |
|---|---|---|
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0087050 A1 | 3/2018 | Zheng et al. |
| 2018/0094298 A1 | 4/2018 | Hindson et al. |
| 2018/0094312 A1 | 4/2018 | Hindson et al. |
| 2018/0094313 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0195112 A1 | 7/2018 | Lebofsky et al. |
| 2018/0216162 A1 | 8/2018 | Belhocine et al. |

FOREIGN PATENT DOCUMENTS

| | | |
|---|---|---|
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| EP | 2635679 B1 | 4/2017 |
| GB | 2097692 B | 5/1985 |
| GB | 2485850 A | 5/2012 |
| JP | S 5949832 A | 9/1984 |
| JP | S60227826 A | 11/1985 |
| JP | 2006-507921 A | 3/2006 |
| JP | 2006-289250 A | 10/2006 |
| JP | 2007015990 A | 1/2007 |
| JP | 2007-268350 A | 10/2007 |
| JP | 2009513948 A | 4/2009 |
| JP | 2009-208074 A | 9/2009 |
| JP | 2012131798 A | 7/2012 |
| WO | WO 1984002000 A1 | 5/1984 |
| WO | WO 1994018218 A1 | 8/1994 |
| WO | WO 1994019101 A1 | 9/1994 |
| WO | WO 1994023699 A1 | 10/1994 |
| WO | WO 1995030782 A1 | 11/1995 |
| WO | WO 96/29629 A2 | 3/1996 |
| WO | WO 96/41011 A1 | 12/1996 |
| WO | WO 1998002237 A1 | 1/1998 |
| WO | WO 1998052691 A1 | 11/1998 |
| WO | WO 99/09217 A1 | 2/1999 |
| WO | WO 99/52708 A1 | 10/1999 |
| WO | WO 00/08212 A1 | 2/2000 |
| WO | WO 2000023181 A1 | 4/2000 |
| WO | WO 00/26412 A1 | 5/2000 |
| WO | WO 2000043766 A1 | 7/2000 |
| WO | WO 2000070095 A2 | 11/2000 |
| WO | WO 2001002850 A1 | 1/2001 |
| WO | WO 01/14589 A2 | 3/2001 |
| WO | WO 02/31203 A2 | 10/2001 |
| WO | WO 01/89787 A2 | 11/2001 |
| WO | WO 2001090418 A1 | 11/2001 |
| WO | WO 2001027610 A3 | 3/2002 |
| WO | WO 02/086148 A1 | 10/2002 |
| WO | WO 2002018949 A3 | 1/2003 |
| WO | WO 2003062462 A2 | 7/2003 |
| WO | WO 2004/002627 A2 | 1/2004 |
| WO | WO 2004/010106 A2 | 1/2004 |
| WO | WO 2005/021151 A1 | 3/2004 |
| WO | WO 2004061083 A2 | 7/2004 |
| WO | WO 2004065617 A2 | 8/2004 |
| WO | WO 2004069849 A2 | 8/2004 |
| WO | WO 2004/091763 A2 | 10/2004 |
| WO | WO 2005/040406 A1 | 10/2004 |
| WO | WO 2004/102204 A1 | 11/2004 |
| WO | WO 2004/103565 A2 | 12/2004 |
| WO | WO 2004/105734 A1 | 12/2004 |
| WO | WO 2005002730 A1 | 1/2005 |
| WO | WO 2005/082098 A2 | 2/2005 |
| WO | WO 2005/023331 A2 | 3/2005 |
| WO | WO 2005/049787 A2 | 6/2005 |
| WO | WO 2006/030993 A1 | 3/2006 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | 2007012638 A1 | 2/2007 |
| WO | WO 2007018601 A1 | 2/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007084192 A2 | 7/2007 |
| WO | 2007093819 A2 | 8/2007 |
| WO | WO 2007/089541 A2 | 8/2007 |
| WO | WO 2008/021123 A1 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2007147079 A2 | 12/2007 |
| WO | WO 2008/091792 A2 | 1/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2008061193 A3 | 11/2008 |
| WO | WO 2008150432 A1 | 12/2008 |
| WO | 2009015296 A1 | 1/2009 |
| WO | WO 2009/005680 A1 | 1/2009 |
| WO | WO 2009/011808 A1 | 1/2009 |
| WO | WO 2009048532 A2 | 4/2009 |
| WO | WO 2009/061372 A1 | 5/2009 |
| WO | WO 2009/085215 A1 | 7/2009 |
| WO | 2009147386 A1 | 12/2009 |
| WO | WO 2010/004018 A2 | 1/2010 |
| WO | WO 2010/033200 A2 | 3/2010 |
| WO | 2010048605 A1 | 4/2010 |
| WO | WO 2010104604 A1 | 9/2010 |
| WO | WO 2010115154 A1 | 10/2010 |
| WO | WO 2010/148039 A2 | 12/2010 |
| WO | WO 2010/151776 A2 | 12/2010 |
| WO | WO 2010117620 A3 | 2/2011 |
| WO | WO 2011028539 A1 | 3/2011 |
| WO | WO 2011/047870 A1 | 4/2011 |
| WO | WO 2011/056546 A1 | 5/2011 |
| WO | WO 2011/066476 A1 | 6/2011 |
| WO | WO 2011074960 A1 | 6/2011 |
| WO | WO 2011140627 A1 | 11/2011 |
| WO | WO 2012/012037 A1 | 1/2012 |
| WO | 2012047889 A2 | 4/2012 |
| WO | WO 2012/048341 A1 | 4/2012 |

(56) References Cited

FOREIGN PATENT DOCUMENTS

| | | |
|---|---|---|
| WO | 2012061832 A1 | 5/2012 |
| WO | WO 2012/083225 A2 | 6/2012 |
| WO | WO 2012/106546 A2 | 8/2012 |
| WO | WO 2012112804 A1 | 8/2012 |
| WO | WO 2012112970 A2 | 8/2012 |
| WO | WO 2012/142611 A2 | 10/2012 |
| WO | WO 2012136734 A1 | 10/2012 |
| WO | WO 2012/149042 A2 | 11/2012 |
| WO | WO 2012148497 A2 | 11/2012 |
| WO | WO 2012/166425 A2 | 12/2012 |
| WO | WO 2013019751 A1 | 2/2013 |
| WO | WO 2013/036929 A1 | 3/2013 |
| WO | WO 2013055955 A1 | 4/2013 |
| WO | WO 2013122996 A1 | 8/2013 |
| WO | WO 2013123125 A1 | 8/2013 |
| WO | WO 2013126741 A1 | 8/2013 |
| WO | WO 2013134261 A1 | 9/2013 |
| WO | WO 2013150083 A1 | 10/2013 |
| WO | WO 2013/177220 A1 | 11/2013 |
| WO | 2013188872 A1 | 12/2013 |
| WO | WO 2014/028537 A1 | 2/2014 |
| WO | WO 2014053854 A1 | 4/2014 |
| WO | 2014071361 A1 | 5/2014 |
| WO | WO 2014074611 A1 | 5/2014 |
| WO | WO 2014/093676 A1 | 6/2014 |
| WO | 2014108810 A2 | 7/2014 |
| WO | 2014140309 A1 | 9/2014 |
| WO | 2014150931 A1 | 9/2014 |
| WO | WO 2014144495 A1 | 9/2014 |
| WO | 2014182835 A1 | 11/2014 |
| WO | 2014189957 A2 | 11/2014 |
| WO | WO 2014210353 A2 | 12/2014 |
| WO | WO 2015044428 A1 | 4/2015 |
| WO | WO 2015164212 A1 | 10/2015 |
| WO | WO 2016040476 A1 | 3/2016 |
| WO | 2016061517 A2 | 4/2016 |
| WO | 2016126871 A2 | 8/2016 |
| WO | 2016187717 A1 | 12/2016 |
| WO | 2016191618 A1 | 12/2016 |
| WO | 2016207647 A1 | 12/2016 |
| WO | 2016207653 A1 | 12/2016 |
| WO | 2016207661 A1 | 12/2016 |
| WO | 2017015075 A1 | 1/2017 |
| WO | 2017025594 A1 | 2/2017 |
| WO | WO 2017053905 A1 | 3/2017 |
| WO | WO 2017075265 A1 | 5/2017 |
| WO | 2017156336 A1 | 9/2017 |
| WO | 2018045186 A1 | 3/2018 |

OTHER PUBLICATIONS

U.S. Appl. No. 14/316,447, filed Jun. 26, 2014.
U.S. Appl. No. 14/316,463, filed Jun. 26, 2014.
U.S. Appl. No. 14/682,952, filed Apr. 9, 2015.
U.S. Appl. No. 14/752,589, filed Jun. 26, 2015.
U.S. Appl. No. 14/752,602, filed Jun. 26, 2015.
U.S. Appl. No. 14/752,641, filed Jun. 26, 2015.
U.S. Appl. No. 14/752,773, filed Jun. 26, 2015.
Altemos et al., "Genomic Characterization of Large Heterochromatic Gaps in the Human Genome Assembly," *PLOS Computational Biology*, May 15, 2014, vol. 10, Issue 5, 14 pages.
Amini et al., "Haplotype-resolved whole genome sequencing by contiguity preserving transposition and combinatorial indexing," *Nature Genetics*, 2014, vol. 46, pp. 1343-1349.
He et al., "Genotyping-by-Sequencing (GBS), an ultimate marker-assisted selection (MAS) tool to accelerate plant breeding," *Front. Plant Sci.*, Sep. 2014, vol. 5, 8 pages.
International Search Report for International Patent Application No. PCT/US2015/058142, dated Feb. 8, 2016, 6 pages.
Peters et al., "Accurate whole-genome sequencing and haplotyping from 10 to 20 human cells," *Nature*, Jul. 12, 2012, vol. 487, pp. 190-195.

Abate et al.., Valve-based flow focusing for drog formation. Appl Phys Left. 2009;94. 3 pages.
Abate, et al.. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Agresti, et al.. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al.., "Formation of dispersions using 'flow focusing' in microchannels", Appln. Phys. Letts. 82:3 364 (2003).
Boone, et al.. Plastic advances microfluidic devices. The devices debuted in silicon and glass, but plastic fabrication may make them hugely successful in biotechnology application. Analytical Chemistry. Feb. 2002; 78A-86A.
Braeckmans et al.., Scanning the Code. Modern Drug Discovery. 2003:28-32.
Bransky, et al.. A microfluidic droplet generator based on a piezo-electric actuator. Lab Chip. Feb. 21, 2009;9(4):516-20. doi: 10.1039/b814810d. Epub Nov. 20, 2008.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in *Escherichia coli* as single-chain imrnunotoxins" Proc. Nat!. Acad. Sci USA 87: 10661070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chou, et al.. Disposable Microdevices for DNA Analysis and Cell Sorting. Proc. Solid-State Sensor and Actuator Workshop, Hilton Head, SC. Jun. 8-11, 1998; 11-14.
Clausell-Tormos et al., "Droplet-based microfluidic platforms for the encapsulation and screening of mammalian cells and multicellular organisms", Chem. Biol. 15:427-437 (2008).
De Bruin et al.., UBS Investment Research. Q-Series®: DNa Sequencing. UBS Securities LLC. Jul. 12, 2007. 15 pages.
Demirci, et al.. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Dowding, et al.. Oil core/polymer shell microcapsules by interNal phase separation from emulsion droplets. II: controlling the release profile of active molecules. Langmuir. Jun. 7, 2005;21(12):5278-84.
Drmanac et al.., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Esser-Kahn, et al.. Triggered release from polymer capsules. Macromolecules. 2011; 44:5539-5553.
Fisher, et al.. A scalable, fully automated process for construction of sequence-ready human exome targeted capture libraries. Genome Biol. 2011;12(1):R1. doi: 10.1186/gb2011-12-1-rl. Epub Jan. 4, 2011.
Freiberg, et al.. Polymer microspheres for controlled drug release. Int J Pharm. Sep. 10, 2004:282(1-2):1-18.
Fu, "A micro fabricated fluorescence-activated cell sorter", Nature Biotech., 17:11091111 (1997).
Fulton et al.., Advanced multiplexed analysis with the FlowMetrix system. Clin Chern. Sep. 1997;43(9): 1749-56.
Garstecki, et al.. Formation of monodisperse bubbles in a microfluidic flow-focusing device. Applied Physics Letters. 2004; 85(13):2649-2651. DOI: 10.1063/1.1796526.
Gartner, et al.. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.

(56) References Cited

OTHER PUBLICATIONS

Ghadessy, et al.. Directed evolution of polymerase function by compartmentalized self-replication. Proc Natl Acad Sci USA. Apr. 10, 2001;98(8):4552-7. Epub Mar. 27, 2001.

Gyarmati et al., "Reversible Disulphide Formation in Polymer Networks: A Versitile Functional Group from Synthesis to Application", European Polymer Journal, 2013, 49, 1268-1286.

Hashimshony, et al.. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

He, "Selective Encapsulation of Single Cells and Subcellular Organelles into Picoliterand Femtoliter-Volume Droplets" ANal. Chern 77: 1539-1544 (2005).

Holtze, et al.. Biocompatible surfactants for water-in-fluorocarbon emulsions. Lab Chip. Oct. 2008;8(10):1632-9. doi: 10.1039/b806706f. Epub Sep. 2, 2008.

Huebner, "Quantitative detection of protein expression in single cells using droplet microfluidics", Chern. Commun 1218-1220 (2007).

Hug, et al.. Measurement of the number of molecules of a single mRNA species in a complex mRNA preparation. J Theor Biol. Apr. 21, 2003;221(4):615-24.

Khomiakov A et al.., [Analysis of perfect and mismatched DNA duplexes by a generic hexanucleotide microchip]. Mol Bioi (Mosk). Jul.-Aug. 2003;37(4):726-41. Russian. Abstract only.

Kim, et al.. Albumin loaded microsphere of amphiphilic poly(ethylene glycol)/ poly(alpha-ester) multiblock copolymer. Eur J Pharm Sci. Nov. 2004;23(3):245-51.

Kim, et al.. Fabrication of monodisperse gel shells and functioNal microgels in microfluidic devices. Angew Chem Int Ed Engl. 2007;46(11):1819-22.

Koster et al.., "Drop-based microfluidic devices for encapsulation of single cells", Lab on a Chip The Royal Soc. of Chern. 8: 1110-1115 (2008).

Kutyavin, et al.. Oligonucleotides containing 2-aminoadenine and 2-thiothymine act as selectively binding complementary agents. Biochemistry. Aug. 27, 1996;35(34):11170-6.

Li, Y., et al.., "PEGylated PLGA Nanoparticles as protein carriers: synthesis, preparation and biodistribution in rats," JourNal of Controlled Release, vol. 71, pp. 203-211 (2001).

Liu, et al.. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.

Liu, et al.. Smart thermo-triggered squirting capsules for nanoparticle delivery. Soft Matter. 2010; 6(16):3759-3763.

Loscertales, I.G., et al.., "Micro/Nano Encapsulation via Electrified Coaxial Liquid Jets," Science, vol. 295, pp. 1695-1698 (2002).

Love, "A microengraving method for rapid selection of single cells producing antigen-specific antibodies", Nature Biotech, 24:6 703 (Jun. 2006).

Marcus. Gene method offers diagnostic hope. The Wall Street Journal. Jul. 11, 2012.

Mazutis, et al.. Selective droplet coalescence using microfluidic systems. Lab Chip. Apr. 24, 2012;12(10):1800-6. doi: 10.1039/c2lc40121e. Epub Mar. 27, 2012.

Merriman, et al.. Progress in ion torrent semiconductor chip based sequencing. Electrophoresis. Dec. 2012;33(23):3397-417. doi: 10.1002/elps.201200424.

Microfluidic ChipShop. Microfluidic product catalogue. Mar. 2005.
Microfluidic ChipShop. Microfluidic product catalogue. Oct. 2009.

Mirzabekov, "DNA Sequencing by Hybridization—a Megasequencing Method and a Diagnostic Tool?" Trends in Biotechnology 12(1): 27-32 (1994).

Mouritzen et al.., Single nucleotide polymorphism genotyping using locked nucleic acid (LNa). Expert Rev Mol Diagn. Jan. 2003;3(1):27-38.

Nguyen, et al.. In situ hybridization to chromosomes stabilized in gel microdrops. Cytometry. 1995; 21:111-119.

Oberholzer, et al.. Polymerase chain reaction in liposomes. Chem Biol. Oct. 1995;2(10):677-82.

Ogawa, et al.. Production and characterization of 0/W emulsions containing cationic droplets stabilized by lecithin-chitosan membranes. J Agric Food Chem. Apr. 23, 2003;51(9):2806-12.

Okushima, "Controlled production of monodisperse double emulsions by two-step droplet breakup in microfluidic devices", Langmuir, 20:9905-9908 (2004).

Perez, C., et al.., "Poly(lactic acid)-poly(ethylene glycol) Nanoparticles as new carriers for the delivery ofplasmid DNa," JourNal of Controlled Release, vol. 75, pp. 211-224 (2001).

Plunkett, et al.. Chymotrypsin responsive hydrogel: application of a disulfide exchange protocol for the preparation of methacrylamide containing peptides. Biomacromolecules. Mar.-Apr. 2005;6(2):632-7.

Ryan, et al.. Rapid assay for mycobacterial growth and antibiotic susceptibility using gel microdrop encapsulation. J Clin Microbiol. Jul. 1995;33(7):1720-6.

Schirinzi et al.., Combinatorial sequencing-by-hybridization: aNalysis of the NFI gene. Genet Test. 2006 Spring;10(1):8-17.

Schmitt, "Bead-based multiplex genotyping of human papillomaviruses", J. Clinical Microbial., 44:2 504-512 (2006).

Shah, "Fabrication of mono disperse thermosensitive microgels and gel capsules in micro fluidic devices", Soft Matter, 4:2303-2309 (2008).

Shimkus, et al.. A chemically cleavable biotinylated nucleotide: usefulness in the recovery of protein-DNA complexes from avidin affinity columns Proc Natl Acad Sci U S A. May 1985:82(9):2593-7.

Simeonov et al.., Single nucleotide polymorphism genotyping using short, fluorescently labeled locked nucleic acid (LNa) probes and fluorescence polarization.

Sorokin et al.., Discrimination between perfect and mismatched duplexes with oligonucleotide gel microchips: role of thermodynamic and kinetic effects during hybridization. J Biomol Struct Dyn. Jun. 2005;22(6):725-34.

Su, et al.., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).

Sun et al.., Progress in research and application of liquid-phase chip technology. Chinese Journal Experimental Surgery. May 2005;22(5):639-40.

Tawfik, et al.. Man-made cell-like compartments for molecular evolution. Nat Biotechnol. Jul. 1998;16(7):652-6.

Theberge, et al.. Microdropelts in microfluidics: an evolving platform for discoveries in chemsitry and biology. Angew Chem Int Ed Engl. Aug. 9, 2010;49(34):5846-68. doi: 10.1002/anie.200906653.

Tubeleviciute, et al.. Compartmentalized self-replication (CSR) selection of Thermococcus litoralis Sh1B DNA polymerase for diminished uracil binding. Protein Eng Des Sel. Aug. 2010;23(8):589-97. doi: 10.1093/protein/gzq032. Epub May 31, 2010.

Wang et al.., Single nucleotide polymorphism discrimiNation assisted by improved base stacking hybridization using oligonucleotide microarrays. Biotechniques. 2003;35:300-08.

Wang, et al.. A novel thermo-induced self-bursting microcapsule with magnetic-targeting property. Chemphyschem. Oct. 5, 2009;10(14):2405-9.

Weaver, "Rapid clonal growth measurements at the single-cell level: gel microdroplets and flow cytometry", Biotechnology, 9:873-877 (1991).

Whitesides, "Soft lithography in biology and biochemistry", Annual Review of Biomedical Engineering, 3:335-373 (2001).

Williams, et al.. Amplification of complex gene libraries by emulsion PCR. Nat Methods. Jul. 2006;3(7):545-50.

Woo, et al.. G/C-modified oligodeoxynucleotides with selective complementarily: synthesis and hybridization properties. Nucleic Acids Res. Jul. 1, 1996;24(13):2470-5.

Xia, "Soft lithography", Annual Review of Material Science, 28: 153-184 (1998).

Yamamoto, et al.. Chemical modification of Ce(IV)/EDTA-base artificial restriction DNa cutter for versatile manipulation of doulbestranded DNa. Nucleic Acids Research. 2007; 35(7):e53.

(56) References Cited

OTHER PUBLICATIONS

Zhang, "Combinatorial marking of cells and organelles with reconstituted fluorescent proteins", Cell, 119:137-144 (Oct. 1, 2004).
Zhang, et al.. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhao, J., et al.., "Preparation of hemoglobin-loaded Nano-sized particles with porous structure as oxygen carriers," Biomaterials, vol. 28, pp. 1414-1422 (2007).
Zimmermann et at., Microscale production of hybridomas by hypoosmolar electrofusion. Hum• Antibodies Hybridomas. Jan. 1992;3(1 ): 14-8.
Zong, et al.. Genome-wide detection of single-nucleotide and copy-number variations of a single human cell. Science. Dec. 21, 2012;338(6114):1622-6. doi: 10.1126/science.1229164.
Makino et al., "Preparation of hydrogel microcapsules: Effects of preparation conditions upon membrane properties," Colloids and Surfaces B: Biointerfaces, vol. 12, Issue 2, Nov. 1998, pp. 97-104.
Nagashima et al., "Preparation of monodisperse poly(acrylamide-co-acrylic acid) hydrogel microspheres by a membrane emulsification technique and their size-dependent surface properties," Colloids and Surfaces B: Biointerfaces, vol. 11, Issues 1-2, Jun. 1998, pp. 47-56.
Frampton et al., "Development and validation of a clinical cancer genomic profiling test based on massively parallel DNA sequencing," *Nature Biotechnology*, online publication Oct. 20, 2013, vol. 31, No. 11, pp. 1023-1031; doi:10.1038/nbt.2696.
Sigma, Straptavidin-agarose (S1638) product information sheet, (2007) www.sigma-aldrich.com.
Stoeckius, et al. "Large-scale simultaneous measurement of epitopes and transcriptomes in single cells." bioRxiv 113068; doi: https://doi.org/10.1101/113068.
Susaki et al., "Whole-Brain Imaging with Single-Cell Resolution Using Chemical Cocktails and Computational Analysis," Cell 157, 726-739 (2014).
Tomer et al., "Advanced Clarity for rapid and high-resolution imaging of intact tissues," Nature Protocols 9, p. 1682-1697 (2014) doi:10.1038/nprot.2014.123.
Wang, et al. Digital karyotyping. Proc Natl Acad Sci U S A. Dec. 10, 2002;99(25):16156-61. Epub Dec. 2, 2002.
Wood AJ, et al. "Targeted genome editing across species using ZFNs and TALENs." Science. 2011;333:307.
Zhang F, et al. "Efficient construction of sequence-specific TAL effectors for modulating mammalian transcription," Nat. Biotechnol. 2011;29:149-153.
Zheng, et al. Massively parallel digital transcriptional profiling of single cells. Nat Commun. Jan. 16, 2017;8:14049. doi: 10.1038/ncomms14049.
Zhu et al. "Hydrogel Droplet Microfluidics for High-Throughput Single Molecule/Cell Analysis," Accounts of Chemical Research Article ASAP. DOI: 10.1021/acs.accounts.6b00370.
Abate, A.R. et al. "Beating Poisson encapsulation statistics using close-packed ordering" Lab on a Chip (Sep. 21, 2009) 9(18):2628-2631.
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous, "Viscosity—Basic concepts" (2004) XP055314117, Retrieved from the Internet: URL:http://lhtc.epfl.ch/webdav/site/lhtc/shared/import/migration/2 VISCOSITY.pdf.
Attia, U.M et al., "Micro-injection moulding of polymer microfluidic devices" Microfluidics and nanofluidics (2009) 7(1):1-28.
Baret et al. "Fluorescence-activated droplet sorting (FADS): efficient microfluidic cell sorting based on enzymatic activity" Lab on a Chip (2009) 9(13):1850-1858.
Brouzes, E et al., "Droplet microfluidic technology for single-cell high-throughput screening" PNAS (2009) 106(34):14195-14200.
Chen, F et al., "Chemical transfection of cells in picoliter aqueous droplets in fluorocarbon oil" Anal. Chem. (2011) 83:8816-8820.
Chokkalingam, V et al., "Probing cellular heterogeneity in cytokine-secreting immune cells using droplet-based microfluidics" Lab Chip (2013) 13:4740-4744.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, L-Y. et al., "Controllable monodisperse multiple emulsions" Angew. Chem. Int. Ed. (2007) 46:8970-8974.
Coufal, et al. L1 retrotransposition in human neural progenitor cells. Nature. Aug. 27, 2009;460(7259):1127-31. doi: 10.1038/nature08248. Epub Aug. 5, 2009.
Doshi, N. et al. "Red blood cell-mimicking synthetic biomaterial particles" PNAS (2009) 106(51):21495-21499.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Eastburn, D.J. et al., "Ultrahigh-throughput mammalian single-cell reverse-transcriptase polymerase chain reaction in microfluidic droplets" Anal. Chem. (2013) 85:8016-8021.
Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fredrickson, C.K. et al., "Macro-to-micro interfaces for microfluidic devices" Lab Chip (2004) 4:526-533.
Gericke, M. et al. "Functional Cellulose Beads: Preparation, Characterization, and Applications" Chem Rev (2013) 113(7):4812-4836.
Granieri, Lucia "Droplet-based microfluidics and engineering of tissue plasminogen activator for biomedical applications" Ph.D. Thesis, Nov. 13, 2009 (131 pages).
Grasland-Mongrain, E. et al. "Droplet coalescence in microlfuidic devices" Internet Citation, 2003, XP002436104, Retrieved from the Internet: URL:http://www.eleves.ens.fr./home/grasland/rapports/stage4.pdf [retrieved on Jun. 4, 2007].
Guo, M.T. et al., "Droplet microfluidics for high-throughput biological assays" Lab Chip (2012) 12:2146-2155.
Hjerten, S. et al. "General methods to render mcaroporous stationary phases nonporous and deformable, exemplified with agarose and silica beads and their use in high-performance ion-exchange and hydrophobic-interaction chromatography of proteins" Chromatographia (Jan. 1991) 31(1-2):85-94.
Ioannidis, N "Manufacturing of agarose-based chromatographic media with controlled pore and particle size" (2009) XP055289233, Retrieved from the Internet: URL: http://etheses.bham.ac.uk/368/3/Ioannidis09PhD.pdf.
Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Kim, J et al., "Rapid prototyping of microfluidic systems using a PDMS/polymer tape composite" Lab Chip (2009) 9:1290-1293.
Klein, et al. Droplet barcoding for single-cell transcriptomics applied to embryonic stem cells. Cell. May 21, 2015; 161:1187-1201.
Lagus, T.P. et al., "A review of the theory, methods and recent applications of high-throughput single-cell droplet microfluidics" J. Phys. D: Appl. Phys. (2013) 46:114005 (21 pages).

(56) References Cited

OTHER PUBLICATIONS

Lee, J-H. et al. "Fluorescent in situ sequencing (FISSEQ) of RNA for gene expression profiling in intact cells and tissues" Nature Protocols (Feb. 12, 2015) 10(3):442-458.
Lowe, Adam J. "Norbornenes and [n]polynorbornanes as molecular scaffolds for anion recognition" Ph.D. Thesis (May 2010). (361 pages).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, D.A. et al., "Injection molded microfluidic chips featuring integrated interconnects" Lab Chip (2006) 6:1346-1354.
Matochko, W.L. et al., "Uniform amplification of phage display libraries in monodisperse emulsions," Methods (2012) 58:18-27.
Moore, J.L. et al., "Behavior of capillary valves in centrifugal microfluidic devices prepared by three-dimensional printing" Microfluid Nanofluid (2011) 10:877-888.
Morgan, et al. Chapter 12: Human microbiome analysis. PLoS Comput Biol. 2012;8(12):e1002808. doi: 10.1371/journal.pcbi. 1002808. Epub Dec. 27, 2012.
Mozhanova, A.A. et al. "Local elastic properties of biological materials studied by SFM" (2003) XP055314108, Retrieved from the Internet: URL:http://www.ntmdt.com/data/media/files/publications/ 2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/ nature09544.
Navin, N.E. "The first five years of single-cell cancer genomics and beyond" Genome Res. (2015) 25:1499-1507.
Novak, R. et al., "Single cell multiplex gene detection and sequencing using microfluidicallygenerated agarose emulsions" Angew. Chem. Int. Ed. Engl. (2011) 50(2):390-395.
Pantel, et al. Detection methods of circulating tumor cells. J Thorac Dis. Oct. 2012;4(5):446-7. doi: 10.3978/j.issn.2072-1439.2012.08. 15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Picot, J. et al. "A biomimetic microfluidic chip to study the circulation and mechanical retention of red blood cells in the spleen" Am J Hematology (Jan. 12, 2015) 90(4):339-345.
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011. 555598. Epub Mar. 1, 2011.
Richardson, T.T. et al. "Novel inhibition of archaeal family-D DNA polymerase by uracil" Nucl Acids Res (2013) 41(7):4207-4218.
Rogozin, I.B. et al. "A highly conserved family of inactivated archaeal B family DNA polymerases" Biology Direct (2008) 3:32-36.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Schmieder, R. et al. "Fast Identification and Removal of Sequence Contamination from Genomic and Metagenomic Datasets" PLoS ONE, (Mar. 9, 2011) 6(3):1-11.
Seiffert, S. et al., "Smart microgel capsules from macromolecular precursors" J. Am. Chem. Soc. (2010) 132:6606-6609.
Shuttleworth, et al. "Recognition of the pro-mutagenic base uracil by family B DNA polymerases from archaea" J Mol Biol (Mar. 26, 2004) 337(3):621-634.
Tayyab, S. et al. "Size exclusion chromatography and size exclusion HPLC of proteins" Biochem Ed, Pergamon, (1991) 19(3):149-152.
Tewhey, R. et al., "Microdroplet-based PCR enrichment for large-scale targeted sequencing" Nature Biotech. (2009) 27(11):1025-1031 and Online Methods (11 pages).
Tonelli, C. et al., "Perfluoropolyether functional oligomers: unusual reactivity in organic chemistry" J. Fluorine Chem. (2002) 118:107-121.
Turner, et al. "Methods for genomic partitioning" Annu Rev Genomics Human Genet. (2009) 10:263-284. doi: 10.1146/annurev-genom-082908-150112. Review.
Wagner, O et al., "Biocompatible fluorinated polyglycerols for droplet microfluidics as an alternative to PEG-based copolymer surfactants" Lab Chip DOI:10.1039/C5LC00823A. (2015).
Zheng, X.Y. et al. "Haplotyping germline and cancer genomes with high-throughput linked-read sequencing" Nature Biotech (Feb. 1, 2016) 34(3):303-311.
Zhu, S. et al., "Synthesis and self-assembly of highly incompatible polybutadienepoly (hexafluoropropoylene oxide) diblock copolymers" J. Polym. Sci. (2005) 43:3685-3694.
Aitman, et al. Copy number polymorphism in Fcgr3 predisposes to glomerulonephritis in rats and humans. Nature. Feb. 16, 2006;439(7078):851-5.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08. 001.
Berkum et al., "Hi-C: A Method to Study the Three-dimensional Architecture of Genomes," J Vis Exp (39), e1896, doi:10.3791/1869 (2010).
Biles et al., Nucl. Acids Res. 32(22):e176 2004.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Browning, S.R. et al. "Haplotype Phasing: Existing Methods and New Developments" NaRevGenet (Sep. 16, 2011) 12(10):703-714.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Choi et al. "Identification of novel isoforms of the EML4-ALK transforming gene in non-small cell lung cancer," Cancer Res (2008) 68:4971-4976.
Christian M, et al. Targeting DNA double-strand breaks with TAL effector nucleases Genetics. (2010) 186:757-761.
Chung et al., "Structural and molecular interrogation of intact biological systems," Nature, May 16, 2013, 23 pages.
Cong, L. et al. "Multiplex Genome Engineering Using CRISPR/Cas Systems" Science (Feb. 15, 2013) 339(6121):819-823. doi:10.1126/ science.1231143.
Cook, et al. Copy-number variations associated with neuropsychiatric conditions. Nature. Oct. 16, 2008;455(7215):919-23. doi: 10.1038/ nature07458.
Co-pending U.S. Appl. No. 15/392,557, filed Dec. 28, 2016.
Co-pending U.S. Appl. No. 15/430,298, filed Feb. 10, 2017.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Co-pending U.S. Appl. No. 15/588,519, filed May 5, 2017.
Co-pending U.S. Appl. No. 15/598,898, filed May 18, 2017.
Dekker et al., "Capturing chromosome conformation," Science 295:1306-1311 (2002).
Dressman et al. "Transforming single DNA molecules into fluorescent magnetic particles for detection and enumeration of genetic variations" PNAS (2003) 100(15):8817-8822.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. "Whole-genomre molecular haplotyping of single cells," Nature Biotechnology, vol. 29 No. 1, Jan. 2011.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Hirsch et al. "Easily reversible desthiobiotin binding to streptavidin, avidin, and other biotin-binding proteins: uses for protein labeling, detection, and isolation" Analytical Biochem (2002) 308.

(56) References Cited

OTHER PUBLICATIONS

Illumina TrueSeq Custom Enrichment Kit, pp. 1-4 (2011-2012).
Kaper et al., PNAS, vol. 110, (Apr. 2013) Supplemental date pp. 1-7.
Karmakar et al., "Organocatalytic removal of formaldehyde adducts from RNA and DNA bases," Nature Chemistry, 2015, doi:10.1038/nchm.2307.
Kebschull et al., "High-Throughput Mapping of Single-Neuron Projections by Sequencing of Barcoded RNA," Neuron, vol. 91, Issue 5, Sep. 7, 2016, p. 975-987.
Kitzman, et al. Noninvasive whole-genome sequencing of a human fetus. Sci Transl Med. Jun. 6, 2012;4(137):137ra76. doi: 10.1126/scitranslmed.3004323.
Kivioj, A. et al., "Counting Absolute Numbers of Molecules Using Unique Molecular Identifiers", Nature Methods 9, 72-74 (2012).
Knight, et al. Subtle chromosomal rearrangements in children with unexplained mental retardation. Lancet. Nov. 13, 1999;354(9191):1676-81.
Korlach, et al., Methods in Enzymology, Real-Time DNA Sequencing from Single Polymerase Molecules, (2010) 472:431-455.
Lee et al., "ACT-PRESTO: Rapid and consistent tissue clearing and labeling method for 3-dimensional (3D) imaging," Sci Rep., Jan. 11, 2016 doi: 10.1038/srep18631.
Lee, J.H. et al. "Highly multiplexed subcellular RNA sequencing in situ" Science (Mar. 21, 2014) 343(6177):1360-1363.
Li, et al. A single-cell-based platform for copy number variation profiling through digital counting of amplified genomic DNA fragments. ACS Appl Mater Interfaces. Mar. 24, 2017. doi:10.1021/acsami.7b03146. [Epub ahead of print].
Lupski. Genomic rearrangements and sporadic disease. Nat Genet. Jul. 2007;39(7 Suppl):S43-7.
Miller, J.C. et al. An improved zinc-finger nuclease architecture for highly specific genome editing. Nat. Biotechnol. 2007;25:778-785.
Nagano et al. "Single cell Hi-C reveals cell-to-cell variability in chromosome structure," Nature, vol. 502, No. 7469, Sep. 25, 2013.
Nextera Enrichment Sample Preparation Guide from Illumina, pp. 1-69 (Feb. 2013).
Oligotex Handbook. For purification of poly A+ RNA from total RNA and directly from cultured cells or tissues as well as purification of polyadenylated in vitro transcripts. Jun. 2012.
Pinto, et al. Functional impact of global rare copy number variation in autism spectrum disorders. Nature. Jul. 15, 2010;466(7304):368-72. doi: 10.1038/nature09146. Epub Jun. 9, 2010.
Porteus, M.H., Baltimore D. Chimeric nucleases stimulate gene targeting in human cells. Science. 2003;300:763.
Ramskold et al. "Full-length mRNA-Seq from single-cell levels of RNA and individual circulating tumor cells" Nature Biotech (2012) 30(8):777-782.
Ran, et al., Genome Engineering Using the CRISPR-Cas9 System, Nature Protocol, (2013), 8(11):2281-2308.
Ropers. New perspectives for the elucidation of genetic disorders. Am J Hum Genet. Aug. 2007;81(2):1 99-207. Epub Jun. 29, 2007.
Rotem, A. et al. "Single-cell ChIP-seq reveals cell subpopulations defined by chromatin state" Nature Biotech (Oct. 12, 2015) 33(11):1165-1172.
Sander JD, et al. Selection-free zinc-finger-nuclease engineering by context-dependent assembly (CoDA). Nat. Methods. 2011;8:67-69.
Sebat, et al. Strong association of de novo copy number mutations with autism. Science. Apr. 20, 2007;316(5823):445-9. Epub Mar. 15, 2007.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
"Portable Water Filters" (http://www.portablewaterfilters.org/water-filter-guide/particle-contaminant-size-chart-microns/) 2015, accessed Oct. 19, 2017. (Year: 2015).

Ahern, "Biochemical, Reagents Kits Offer Scientists Good Return on Investment" The Scientist (1995) 9(15):1-7.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi:10.1038/nbt.3662. Epub Aug. 29, 2016.
Boulanger, et al, "Massively parallel haplotyping on microscopic beads for the high-throughput phase analysis of single molecules", PLoS One, vol. 7:1-10, 2012.
Brown, K., Targeted Sequencing Using Droplet-Based Microfluidics, RainDance Technologies, 2009, 1-18.
Buchman, GW et al. "Selective RNA amplification: a novel method using dUMP-containing primers and uracil DNA glycosylase" PCR Methods Appl. Aug. 1993; 3(1):28-31.
Burns, J.R. et al. "The intensification of rapid reactions in multiphase systems using slug flow in capillaries" Lab Chip. (Sep. 2001) 1(1):10-15.
Burns, M.A. et al. "An Integrated Nanoliter DNA Analysis Device" Science (1998) 282:484-487.
Burns, M.A. et al. "Microfabricated structures for integrated DNA analysis" PNAS (1996) 93(11):5556-5561.
Casbon, et al, "Reflex: intramolecular barcoding of long-range PCR products for sequencing multiple pooled DNAs", Nucleic Acids Res., pp. 1-6, 2013.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/693,374, filed Aug. 31, 2017.
Co-pending U.S. Appl. No. 15/717,840, filed Sep. 27, 2017.
Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/719,459, filed Sep. 28, 2017.
Co-pending U.S. Appl. No. 15/720,085, filed Sep. 29, 2017.
Co-pending U.S. Appl. No. 15/831,847, filed Dec. 5, 2017.
Curcio, M. "Improved Techniques for High-Throughput Molecular Diagnostics" Royal Institute of Technology (2002) Ph.D. Thesis.
Damean, N. et al. "Simultaneous measurement of reactions in microdroplets filled by concentration gradients" Lab Chip (Jun. 21, 2009) 9(12):1707-1713.
Dressman et al. Supplementary Information pp. 1-2 of article published 2003, PNAS 100(15:8817-22).
Hamilton, A.J. "microRNA in erythrocytes" Biochem. Soc. Trans. (2010) 38, 229-231.
Han, X. et al. "CRISPR-Cas9 delivery to hard-to-transfect cells via membrane deformation" Science Advances (2015) 1(7): E1500454 (8 pages).
Hiatt, et al, "Parallel, tag-directed assembly of locally derived short sequence reads", Nat Methods., 7:119-122, 2010.
Hosokawa, M. et al. "Massively parallel whole genome amplification for single-cell sequencing using droplet microfluidics" Scientific Reports (2017) 7:5199 (11 pages).
Hosono S. et al. "Unbiased whole-genomeamplification directly from clinical samples" Genome Res. May 2003; 13(5):954-64. Epub Apr. 14, 2003.
Imburgio, et al, "Studies of promoter recognition and start site selection by T7 RNA polymerase using a comprehensive collection of promoter variants", Biochemistry., 39:10419-30, 2000.
Kamperman, T. et al. "Centering Single Cells in Microgels via Delayed Crosslinking Supports Long-Term 3D Culture by Preventing Cell Escape" Small. Jun. 2017;13(22). doi: 10.1002/smll.201603711. Epub Apr. 28, 2017.
Katsura, S. et al. "Indirect micromanipulation of single molecules in water-in-oil emulsion" Electrophoresis (2001) 22(2):289-293.
Kenis, P.J. et al. "Microfabrication inside capillaries using multiphase laminar flow patterning" Science (Jul. 2, 1999);285(5424):83-85.
Kirkness et al. "Sequencing of isolated sperm cells for direct haplotyping of a human genome," Genome Res (2013) 23:826-832.

(56) References Cited

OTHER PUBLICATIONS

Kitzman et al. "Haplotype-resolved genome sequencing of a Gujarati Indian individual." Nat Biotechnol (2011) 29:59-63.
Kozarewa, et al, "96-plex molecular barcoding for the Illumina Genome Analyzer", Methods Mol Biol., 733:279-98, 2011.
Kozarewa, I. et al. "Amplification-free Illumina sequencing-library preparation facilitates improved mapping and assembly of GC-biased genomes", Nat Methods., 6: 291-5, 2009.
Kwok et al, "Single-molecule analysis for molecular haplotyping", Hum Mutat., 23:442-6, 2004.
Lagally, E.T. et al. "Single-Molecule DNA Amplification and Analysis in an Integrated Microfluidic Device" Anal. Chem. (2001) 73(3):565-570.
Laird et al, Hairpin-bisulfite PCR: Assessing epigenetic methylation patterns on complementary strands of individual DNA molecules, 2004, PNAS, 101, 204-209.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lienemann, P.S. et al. "Single cell-laden protease-sensitive microniches for long-term culture in 3D" LabChip (2017) 17(4):727-737.
Linch, et al. Bone marrow processing and cryopreservation. Journal of Clinical Pathology; Feb. 1982, vol. 35, No. 2; pp. 186-190.
Lo, et al. On the design of clone-based haplotyping. Genome Biol. 2013;14(9):R100.
Lundin, et al, "Hierarchical molecular tagging to resolve long continuous sequences by massively parallel sequencing", Sci Rep., 3:1186, 2003.
Man, P. "Monolithic structures for integrated microfluidic analysis" (2001) Dissertation.
Maricic, T. et al. "Optimization of 454 sequencing library preparation from small amounts of DNA permits sequence determination of both DNA strands" Biotechniques. Jan. 2009; 46(1):51-2, 54-7.
miRNA (http://www.exiqon.com/what-are-microRNAs) accessed Oct. 19, 2017 (Year: 2017).
Myllykangas et al., Targeted Sequencing Library Preparation by Genomic DNA Circularization, BMC Biotechnology, 2011, 11(122), 1-12.
Nisisako, T. et al. "Droplet formation in a microchannel network" Lab on a Chip (2002) 2:24-26.
Nisisako, T. et al. "Droplet Formation in a Microchannel on PMMA Plate" Abstract.
Orakdogen, N. "Novel responsive poly(N,N-dimethylaminoethyl methacrylate) gel beads: preparation, mechanical properties and pH-dependent swelling behavior" J Polym Res (2012) 19:9914 (Year: 2012).
Oyola, et al, "Optimizing Illumina next-generation sequencing library preparation for extremely AT-biased genomes", BMC Genomics., 13:1, 2012.
Perrott, Jimmy. Optimization and Improvement of Emulsion PCR for the Ion Torrent Next-Generation Sequencing Platform. (2011) Thesis.
Rakszewska, A. et al. "One drop at a time: toward droplet microfluidics as a versatile tool for single-cell analysis" NPG Asia Materials (2014) 6(10):e133 (12 pages).
Ramsey, J.M. "The burgeoning power of the shrinking laboratory" Nature Biotech (1999) 17:1061-1062.
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Roche "Using Multiplex Identifier (MID) Adaptors for the GS FLX Titanium Chemistry Basic MID Set" Genome Sequencer FLX System, Technnical Bulletin 004-2009, (Apr. 1, 2009) pp. 1-7. URL:http://454.com/downloads/my454/documentation/technical-bulletins/TCB-09004 Using MultiplexIdentifierAdaptorsForTheGS FLXTitaniumSeriesChemistry-BasicMIDSet.pdf.
Roche "Using Multiplex Identifier (MID) Adaptors for the GS FLX Titanium Chemistry Extended MID Set" Genome Sequencer FLX System, Technnical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGS FLXTitaniumChemistry-ExtendedMIDSet.pdf.
Rodrigue, S. et al. "Whole Genome Amplification and De novo Assembly of Single Bacterial Cells" PLoS ONE, (2009) 4(9):1-10.
Schubert, et al. "Microemulsifying fluorinated oils with mixtures of fluorinated an hydrogenated surfactants" Colloids and Surfaces A: Physicochemical and Engineering Aspects (1994) 84:97-106.
Schwartz; et al., "Capturing native long-range contiguity by in situ library construction and optical sequencing", PNAS (Nov. 2012), 109(46)18749-18754.
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Skerra, A. "Phosphorothioate primers improve the amplification of DNA sequences by DNA polymerases with proofreading activity" Nucleic Acids Res. Jul. 25, 1992; 20(14):3551-4.
Song, H. et al. "Reactions in Droplets in Microfluidic Channels" Angew. Chem. Int. Ed. (2006) 45:7336-7356.
Stoeckius et al. "Simultaneous epitope and transcriptome measurement in single cells" Nature Methods (Jul. 31, 2017) Supplemental Materials.
Tewhey et al., Supplementary Materials, Nature Biotechnology, 2009, 27(11), 1-22.
Thorsen, T. et al. "Dynamic Pattern Formation in a Vesicle-Generating Microfluidic Device" Phys Rev Letts (Apr. 30, 2001) 86(18):4163-4166.
Turner, et al, "Assaying chromosomal inversions by single molecule haplotyping", Nat Methods., 3:439-445, 2006.
Turner, et al, "High-throughput haplotype determination over long distances by haplotype fusion PCR and ligation haplotyping", Nat Protoc., 4:1771-83, 2009.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wang; et al., "Self-Formed Adaptor PCR: a Simple and Efficient Method for Chromosome Walking", Applied and Environmental Microbiology (Aug. 2007), 73(15):5048-5051.
Ward, T. et al. "Microfluidic flow focusing: drop size and scaling in pressure versus flow-rate-driven pumping" Electrophoresis (2005) 26(19):3716-3724.
Weigl, B.H. et al. "Microfluidic Diffusion-Based Separation and Detection" Science (Jan. 15, 1999) 283(5400):346-347.
Wiseman, R.W. et al. "Major histocompatibility complex genotyping with massively parallel pyrosequencing" Nature Medicine (Oct. 11, 2009) 15(11):1322-1326.
Xi, L. et al. "New library construction methods for single-cell genomes" PLOS (2017) 12(7):e0181163.
Xiao, et al, "Determination of haplotypes from single DNA molecules: a method for single-molecule barcoding", Hum Mutat., 28:913-21, 2007.
Yan, Pu et al. "Rapid on-step construction of hairpin RNA" Biochem and Biophys Res Comm (Jun. 12, 2009) 383(4):464-468.
Zeng, Y. et al. "High-Performance Single Cell Genetic Analysis Using Microfluidic Emulsion Generator Arrays" Analytical Chemistry (Apr. 15, 2010) 82(8):3183-3190.
Zhang. Genomics of inherited bone marrow failure and myelodysplasia. Dissertation [online]. University of Washington. 2015 [Retrieved on May 3, 2017].
Lai, H-H et al. "Characterization and use of laser-based lysis for cell analysis on-chip" J.R. Soc. Interface (2008) 5: S113-S121.
Lake, et al. "Integrative Single-Cell Analysis by Transcriptional and Epigenetic States in Human Adult Brain". Apr. 19, 2017. doi: https://doi.org/10.1101/128520.

(56) References Cited

OTHER PUBLICATIONS

Lander, et al. Initial sequencing and analysis of the human genome. Nature, 409 (Feb. 15, 2001): 860-921.
Lasken et al. "Archaebacterial DNA Polymerases Tightly Bind Uracil-containing DNA" The Journal of Biological Chemistry (1996) 271 (30):17692-17696.
Lee, K. Y. et al. "Alginate: properties and biomedical applications" Prog Polym Sci. Jan. 2012 ; 37(1): 106-126.
Lennon et al. "A scalable, fully automated process for construction of sequence-ready barcoded libraries for 454." Genome Biology 11:R15 (2010).
Macaulay, et al. Single-Cell Multiomics: Multiple Measurements from Single Cells. Trends in Genetics 33.2 (2017): 155-168. PMC. Web. Dec. 18, 2017.
Macaulay; et al., "G&T-seq: parallel sequencing of single-cell genomes and transcriptomes." Nature Methods, 2015, p. 1-7.
McGinnis, C.S. et al. "MULTI-seq: Scalable sample multiplexing for single-cell RNA sequencing using lipi-tagged indices" bioRxiv (2018) doi: http://dx.doi.org/10.1101/387241.
Miller-Stephenson Chemicals 157 FS Series catalog, www.miller-stephenon.com.
Morimoto, Y. et al. "Monodisperse semi-permeable microcapsules for continuous observation of cells" LabChip (2009) 9(15):2217-2223.
Morton. Parameters of the human genome. Apr. 23, 1991. Proceedings of the National Academy of Sciences of the United States of America, 88: 7474-7476.
Narayanan, J. et al. "Determination of agarose gel pore size: Absorbance measurements vis a vis other techniques" Journal of Physics: Conference Series 28 (2006) 83-86.
National Human Genome Research Institute (NHGRI). The Human Genome Project Completion: Frequently Asked Questions. Last Updated: Oct. 30, 2010.
Park. ChIP-seq: advantages and challenges of a maturing technology. Nature Reviews Genetics vol. 10, pp. 669-680 (2009).
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Qiagen. Omniscript Reverse Transcription Handbook. Oct. 2010.
Sakaguchi et al. "Cautionary Note on the Use of dUMP-Containing PGR Primers with Pfu and VentR". BioTechniques (1996) 21(3):369-370.
Savva et al. "The structural basis of specific base excision repair by uracil-DNA glycosylase" Nature (1995) 373:487-493.
Seiffert, et al. Microfluidic fabrication of smart microgels from macromolecular precursors. 2010. Polymer.
Shaikh, et al. A modular microfluidic architecture for integrated biochemical analysis. Proc Natl Acad Sci U S A. Jul. 12, 2005;102(28):9745-50. Epub Jun. 28, 2005.
Simon, et al., "Using formaldehyde-assisted isolation of regulatory elements (FAIRE) to isolate active regulatory DNA", Nature Protocols, 2012, 7(2): 256-267.
Smith, A.M. et al. "Highly-multiplexed barcode sequencing: an efficient method for parallel analysis of pooled samples" Nucl Acids Res (2010) 38(13):e142 Epub May 11, 2010.
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Spormann Laboratory, Polymerase Chain Reaction (PCR), Alfred Spormann Laboratory, 2009, 1-3.
Syed, F. et al. Nature Methods (Nov. 2009) 2 pages.
ThermoFisher, Protocols, M-270 Streptavidin, ThermoFisherScientific, 2007, 1-5. (Year: 2007).
Wong, et al. "Multiplexed Barcoded CRISPR-Cas9 Screening Enabled by CombiGEM" PNAS (2016) 113:2544-2549.
Xia and Whitesides, Soft Lithography, Angew. Chem. Int. Ed. 37:550-575 (1998).
Zentner, et al. Surveying the epigenomic landscape, one base at a time. Genome Biol. Oct. 22, 2012;13(10):250. doi: 10.1186/gb4051.
Zhou, Y. et al. "Development of an enzyme activity screening system for ($\beta$-glucosidase-displaying yeasts using calcium alginatemicrobeads and flow sorting" Appl Microbiol Biotechnol (2009) 84:375-382.
Zhu, YY et al. "Reverse transcriptase template switching: a SMART approach for full-length cDNA library construction" Biotechniques (2001) 30(4):892-897.
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilizedperturb-seq-approach/.
Adamson et al., "Production of arrays of chemically distinct nanolitre plugs via repeated splitting in microfluidic devices", Lab Chip 6(9): 1178-1186 (Sep. 2006).
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adey, et al. Rapid, low-input, low-bias construction of shotgun fragment libraries by high-density in vitro transposition. Genome Biology 11 :R119 (2010).
Adey, et al., "Ultra-low-input, tagmentation-based whole-genome bisulfite sequencing", Genome Research, 2012, 22 ;6): 1139-1143.
Ason et al. DNA sequence bias during Tn5 transposition. Journal of molecular biology 335.5 (2004): 1213-1225.
Bjornsson et al., Intra-individual change over time in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatoryvariation. Nature. Jul. 23, 2015;523(7561):486-90. doi: 10.1038/nature14590. Epub Jun. 17, 2015.
Carruccio et al. "Nextera Technolgoy for NGS DNA Library Preparation: Simultaneous Fragmentation and Tagging by In Vitro Transposition" Nextera Technology, 2009 16-3, 1-3 (Year: 2009).
Caruccio, N., "Preparation of Next-Generation Sequencing Libraries Using Nextera Technology: Simultaneous DNA Fragmentation and Adaptor Tagging by In Vitro Transposition." Ch. 17 Methods in Microbiology 733:241 (2011).
Chang et al. "Droplet-based microfluidic platform for heterogeneous enzymatic assays" LabChip (2013) 13:1817-1822.
Clark, et al. Single-cell epigenomics: powerful new methods for understanding gene regulation and cell identity. Genome Biol. Apr. 18, 2016;17:72. doi: 10.1186/s13059-016-0944-x.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Co-pending U.S. Appl. No. 16/045,474, filed Jul. 25, 2018.
Co-pending U.S. Appl. No. 16/052,431, filed Aug. 1, 2018.

(56) References Cited

OTHER PUBLICATIONS

Co-pending U.S. Appl. No. 16/052,486, filed Aug. 1, 2018.
Co-pending U.S. Appl. No. 16/056,231, filed Aug. 6, 2018.
Cusanovich, et al. Supplementary materials for Multiplex single-cell profiling of chromatin accessibility by combinatorial cellular indexing. Science. May 22, 2015;348(6237):910-4. doi:10.1126/science.aab1601. Epub May 7, 2015.
Cusanovich; et al., "Multiplex single-cell profiling of chromatin accessibility by combinatorial cellular indexing." Sciencexpress, May 7, 2014, p. 1-9.
Depristo, M.A. et al. "A framework for variation discovery and genotyping using next-generation DNA sequencing data" Nature Genetics (2011) 43(5):491-498.
Dey, et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
EP14800805.5 Extended Search Report dated Jan. 23, 2017.
Gangadharan et al., DNA transposon Hermes insert into DNA in nucleosome-free regions in vivo, Proc nat Ad Sci, Dec. 21, 2010, vol. 107, No. 51, pp. 1966-1972.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/i_ymeth.2014.10.010. Epub Oct. 22, 2014.
Han, S-E et al. "Targeted Sequencing of Cancer-Related Genes in Colorectal Cancer Using Next-Generation Sequencing" PLOS One (2013) 8(5):e64271.
Haring, et al. Chromatin immunoprecipitation: optimization, quantitative analysis and data normalization. Plant Methods. 2007; 3: 11.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Joneja, A. et al. "Linear nicking endonuclease-mediated strand-displacement DNA amplification" Anal Biochem (2011) 414:58-69.
JPK "Determining the elastic modulus of biological samples using atomic force microscopy" (https://www.jpk.com/app-technotes-img/AFM/pdf/jpk-app-elastic-modulus. 14-1.pdf) 2009, pp. 1-9 (Year: 2009).
Knapp, M. et al. "Generating barcoded libraries for multiplex high-throughput sequencing" Methods Mol Biol (2012) 840:155-170 Epub Dec. 8, 2011.
Kolodeziejczyk et al., "The technology and biology of single-cell RNA sequencing", Molecular Cell, vol. 58 (May 21, 2015).

* cited by examiner

METHODS AND COMPOSITIONS FOR TARGETED NUCLEIC ACID SEQUENCING

CROSS-REFERENCE TO RELATED APPLICATIONS

This application is a continuation of U.S. application Ser. No. 14/927,297, filed Oct. 29, 2015, which claims the benefit of U.S. Provisional Application No. 62/072,164, filed Oct. 29, 2014, each of which is expressly incorporated herein by reference in their entirety for all purposes.

BACKGROUND OF THE INVENTION

The ability to sequence genomes accurately and rapidly is revolutionizing biology and medicine. The study of complex genomes, and in particular, the search for the genetic basis of disease in humans, involves genetic analysis on a massive scale. Such genetic analysis on a whole genome level is costly not only monetarily but also in time and labor. These costs increase with protocols involving analyses of separate individual DNA samples. Sequencing (and re-sequencing) of polymorphic areas in the genome that are linked to disease development will contribute greatly to the understanding of diseases, such as cancer, and therapeutic development and will help meet the pharmacogenomics challenge to identify the genes and functional polymorphisms associated with the variability in drug response. Screens for numerous genetic markers performed for populations large enough to yield statistically significant data are needed before associations can be made between a given genotype and a particular disease.

One way to reduce the costs associated with genome sequencing while retaining the benefits of genomic analysis on a large scale is to perform high throughput, high accuracy sequencing on targeted regions of the genome. A widely used approach captures much of the entire protein coding region of a genome (the exome), which makes up about 1% of the human genome, and has become a routine technique in clinical and basic research. Exome sequencing offers advantages over whole genome sequencing: it is significantly less expensive, is more easily understood for functional interpretation, is significantly faster to analyze, makes very deep sequencing affordable, and results in a dataset that is easier to manage. A need exists for methods, systems and compositions for the enrichment of target regions of interest for high accuracy and high throughput sequencing and genetic analysis.

SUMMARY OF THE INVENTION

Accordingly, the present invention provides methods, systems and compositions for obtaining sequence information for targeted regions of the genome.

In some aspects, the present disclosure provides a method for sequencing one or more selected portions of a genome, the method generally including the steps of: (a) providing starting genomic material, (b) distributing individual nucleic acid molecules from the starting genomic material into discrete partitions such that each discrete partition contains a first individual nucleic acid molecule; (c) fragmenting the individual nucleic acid molecules in the discrete partitions to form a plurality of fragments, where each of the fragments further includes a barcode, and where fragments within a given discrete partition each include a common barcode, thereby associating each fragment with the individual nucleic acid molecule from which it is derived; (d) providing a population enriched for fragments including at least a portion of the one or more selected portions of the genome; (e) obtaining sequence information from the population, thereby sequencing one or more selected portions of a genome.

In further embodiments and in accordance with the above, providing the population enriched for fragments including at least a portion of the one or more selected portions of the genome includes the steps of (i) hybridizing probes complementary to regions in or near the one or more selected portions of the genome to the fragments to form probe-fragment complexes; and (ii) capturing probe-fragment complexes to a surface of a solid support; thereby enriching the population with fragments including at least a portion of the one or more selected portions of the genome. In yet further embodiments, the solid support includes a bead. In still further embodiments, the probes include binding moieties and the surface include capture moieties, and the probe-fragment complexes are captured on the surface through a reaction between the binding moieties and the capture moieties. In further examples, the capture moieties include streptavidin and the binding moieties include biotin. In still further examples, the capture moieties comprise streptavidin magnetic beads and the binding moieties comprise biotinylated RNA library baits.

In some embodiments and in accordance with any of the above, the methods of the invention include the use of capture moieties that are directed to whole or partial exome capture, panel capture, targeted exon capture, anchored exome capture, or tiled genomic region capture.

In yet further embodiments and in accordance with any of the above, the methods disclosed herein include an obtaining step that includes a sequencing reaction. In further embodiments, the sequencing reaction is a short read-length sequencing reaction or a long read-length sequencing reaction. In still further examples, the sequencing reaction provides sequence information on less than 90%, less than 75%, or less than 50% of the starting genomic material.

In still further embodiments, the methods described herein further include linking two or more of the individual nucleic acid molecules in an inferred contig based upon overlapping sequences of the isolated fragments, wherein the inferred contig comprises a length N50 of at least 10 kb, 20 kb, 40 kb, 50 kb, 100 kb, or 200 kb.

In yet further examples and in accordance with any of the above, the methods disclosed herein further include linking two or more of the individual nucleic acid molecules in a phase block based upon overlapping phased variants within the sequences of the isolated fragments, where the phase block comprises a length N50 of at least 10 kb, of at least 20 kb, of at least 40 kb, of at least 50 kb, of at least 100 kb or of at least 200 kb.

In still further embodiments and in accordance with any of the above, the methods disclosed herein provide sequence information from selected portions of the genome that together cover an exome. In yet further embodiments, the individual nucleic acid molecules in the discrete partitions include genomic DNA from a single cell. In still further embodiments, the discrete partitions each include genomic DNA from a different chromosome.

In further aspects, the present disclosure provides a method of obtaining sequence information from one or more targeted portions of a genomic sample. Such a method includes without limitation the steps of: (a) providing individual first nucleic acid fragment molecules of the genomic sample in discrete partitions; (b) fragmenting the individual first nucleic acid fragment molecules within the discrete partitions to create a plurality of second fragments from each of the individual first nucleic acid fragment molecules; (c) attaching a common barcode sequence to the plurality of the second fragments within a discrete partition, such that each of the plurality of second fragments are attributable to the discrete partition in which they are contained; (d) applying a library of probes directed to the one or more targeted portions of the genomic sample to the second fragments; (e) conducting a sequencing reaction to identify sequences of the plurality of second fragments that hybridized to the library of probes, thereby obtaining sequence information from the one or more targeted portions of the genomic sample. In further embodiments, the library of probes are attached to binding moieties, and before the conducting step (e), the second fragments are captured on a surface comprising capture moieties through a reaction between the binding moieties and the capture moieties. In still further embodiments and prior to the conducting step (e), the second fragments are amplified before or after the second fragments are captured on the surface. In yet further embodiments, the binding moieties comprise biotin and the capture moieties comprise streptavidin. In still further embodiments, the sequencing reaction is a short read, high accuracy sequencing reaction. In still further embodiments, the second fragments are amplified such that the resultant amplification products are capable of forming partial or complete hairpin structures.

In further aspects and in accordance with any of the above, the present disclosure provides methods for obtaining sequence information from one or more targeted portions of a genomic sample while retaining molecular context. Such methods include the steps of: (a) providing starting genomic material; (b) distributing individual nucleic acid molecules from the starting genomic material into discrete partitions such that each discrete partition contains a first individual nucleic acid molecule; (c) fragmenting the first individual nucleic acid molecules in the discrete partitions to form a plurality of fragments; (d) providing a population enriched for fragments that include at least a portion of the one or more selected portions of the genome; (e) obtaining sequence information from the population, thereby sequencing one or more targeted portions of the genomic sample while retaining molecular context. In further embodiments, prior to the obtaining step (e), the plurality of fragments are tagged with a barcode to associate each fragment with the discrete partition in which it was formed. In still further embodiments, the individual nucleic acid molecules in step (b) are distributed such that molecular context of each first individual nucleic acid molecule is maintained.

In some aspects, the present disclosure provides methods of obtaining sequence information from one or more targeted portions of a genomic sample. Such methods include without limitation steps of (a) providing individual nucleic acid molecules of the genomic sample; (b) fragmenting the individual nucleic acid molecules to form a plurality of fragments, where each of the fragments further includes a barcode, and where fragments from the same individual nucleic molecule have a common barcode, thereby associating each fragment with the individual nucleic acid molecule from which it is derived; (c) enriching the plurality of fragments for fragments containing the one or more targeted portions of the genomic sample; and (d) conducting a sequencing reaction to identify sequences of the enriched plurality of fragments, thereby obtaining sequence information from the one or more targeted portions of the genomic sample. In further embodiments, the enriching step including applying a library of probes directed to the one or more targeted portions of the genomic sample. In yet further embodiments, the library of probes are attached to binding moieties, and prior to the conducting step, the fragments are captured through a reaction between the binding moieties and the capture moieties. In exemplary embodiments, the reaction between the binding moieties and the capture moieties immobilizes the fragments on a surface.

DETAILED DESCRIPTION OF THE INVENTION

Figure 1:
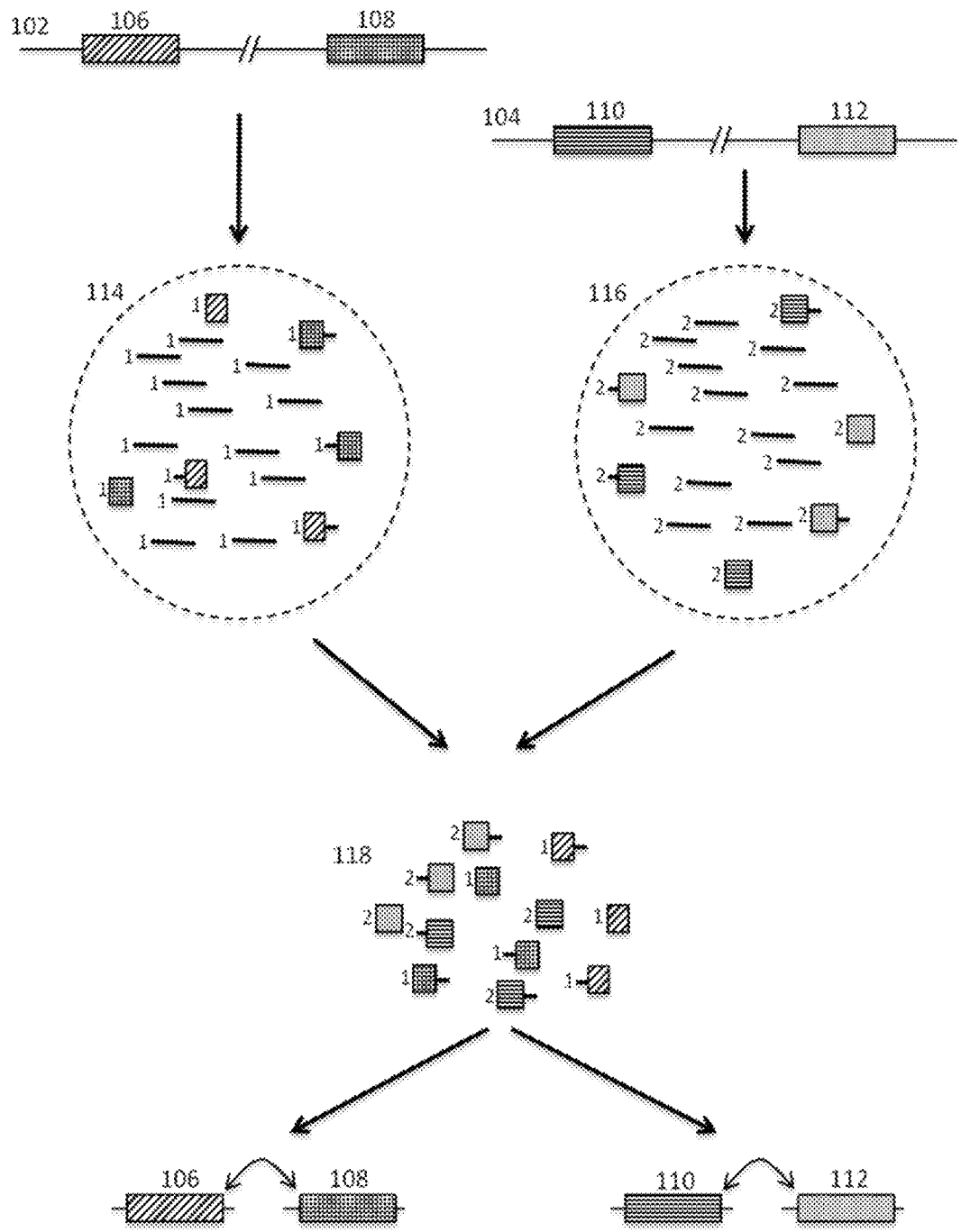
FIG. 1 provides a schematic illustration of identification and analysis of targeted genomic regions using conventional processes versus the processes and systems described herein.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry,* $5^{th}$ Ed. W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method"

includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

I. Overview

This disclosure provides methods, compositions and systems useful for characterization of genetic material. In particular, the methods, compositions and systems described herein provide genetic characterization of targeted regions of a genome, including without limitation particular chromosomes, regions of chromosomes, all exons (exomes), portions of exomes, specific genes, panels of genes (e.g., kinomes or other targeted gene panels), intronic regions, tiled portions of a genome, or any other chosen portion of a genome.

In general, the methods and systems described herein accomplish targeted genomic sequencing by providing for the determination of the sequence of long individual nucleic acid molecules and/or the identification of direct molecular linkage as between two sequence segments separated by long stretches of sequence, which permit the identification and use of long range sequence information, but this sequencing information is obtained using methods that have the advantages of the extremely low sequencing error rates and high throughput of short read sequencing technologies. The methods and systems described herein segment long nucleic acid molecules into smaller fragments that can be sequenced using high-throughput, higher accuracy short-read sequencing technologies, and that segmentation is accomplished in a manner that allows the sequence information derived from the smaller fragments to retain the original long range molecular sequence context, i.e., allowing the attribution of shorter sequence reads to originating longer individual nucleic acid molecules. By attributing sequence reads to an originating longer nucleic acid molecule, one can gain significant characterization information for that longer nucleic acid sequence that one cannot generally obtain from short sequence reads alone. This long range molecular context is not only preserved through a sequencing process, but is also preserved through the targeted enrichment process used in targeted sequencing approaches described herein, where no other sequencing approach has shown this ability.

In general, sequence information from smaller fragments will retain the original long range molecular sequence context through the use of a tagging procedure, including the addition of barcodes as described herein and known in the art. In specific examples, fragments originating from the same original longer individual nucleic acid molecule will be tagged with a common barcode, such that any later sequence reads from those fragments can be attributed to that originating longer individual nucleic acid molecule. Such barcodes can be added using any method known in the art, including addition of barcode sequences during amplification methods that amplify segments of the individual nucleic acid molecules as well as insertion of barcodes into the original individual nucleic acid molecules using transposons, including methods such as those described in Amini et al., Nature Genetics 46: 1343-1349 (2014) (advance online publication on Oct. 29, 2014), which is hereby incorporated by reference in its entirety for all purposes and in particular for all teachings related to adding adaptor and other oligonucleotides using transposons. Once nucleic acids have been tagged using such methods, the resultant tagged fragments can be enriched using methods described herein such that the population of fragments represents targeted regions of the genome. As such, sequence reads from that population allows for targeted sequencing of select regions of the genome, and those sequence reads can also be attributed to the originating nucleic acid molecules, thus preserving the original long range molecular sequence context. The sequence reads can be obtained using any sequencing methods and platforms known in the art and described herein.

In addition to providing the ability to obtain sequence information from targeted regions of the genome, the methods and systems described herein can also provide other characterizations of genomic material, including without limitation haplotype phasing, identification of structural variations, and identifying copy number variations, as described in co-pending U.S. application Ser. Nos. 14/752,589 and 14/752,602, both filed on Jun. 26, 2015), which are herein incorporated by reference in their entirety for all purposes and in particular for all written description, figures and working examples directed to characterization of genomic material.

Methods of processing and sequencing nucleic acids in accordance with the methods and systems described in the present application are also described in further detail in U.S. Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material.

In general, as shown in FIG. 1, the methods and systems described herein may be used to characterize nucleic acids. In particular, as shown, two discrete individual nucleic acids 102 and 104 are illustrated, each having a number of regions of interest, e.g., region 106 and 108 in nucleic acid 102, and regions 110 and 112 in nucleic acid 104. The regions of interest in each nucleic acid are linked within the same nucleic acid molecule, but may be relatively separated from each other, e.g., more than 1 kb apart, more than 5 kb apart, more than 10 kb apart, more than 20 kb apart, more than 30 kb apart, more than 40 kb apart, more than 50 kb apart, and in some cases, as much as 100 kb apart. The regions may denote individual genes, gene groups, exons, or simply discrete and separate parts of the genome. Solely for ease of discussion, the regions shown in FIG. 1 will be referred to as exons 106, 108, 110 and 112. As shown, each nucleic acid 102 and 104 is separated into its own partition 114 and 116, respectively. As noted elsewhere herein, these partitions are, in many cases, aqueous droplets in a water in oil emulsion. Within each droplet, portions of each fragment are copied in a manner that preserves the original molecular context of those fragments, e.g., as having originated from the same molecule. As shown, this is achieved through the inclusion in each copied fragment of a barcode sequence, e.g., barcode sequence "1" or "2" as illustrated, that is representative of the droplet into which the originating fragment was partitioned. For whole genome sequence analysis applications, one could simply pool all of the copied fragments and their associated barcodes, in order to sequence and reassemble the full range sequence information from each of the originating nucleic acids 102 and 104. However, in many cases, it is more desirable to only analyze specific targeted portions of the overall genome, e.g., the exome, specific genes, or the like, in order to provide greater focus on scientifically relevant portions of the genome, and to minimize the time and expense of performing sequencing on less relevant or irrelevant portions of the genome.

In accordance with the methods described herein, target enrichment steps may be applied to the libraries of barcoded sequence fragments in order to "pull down" the sequences associated with the desired targets. These may include exon targeted pull downs, gene panel specific targeted pull downs, or the like. A large number of targeted pull down kits that allow for the enriched separation of specific targeted regions of the genome are commercially available, such as the Agilent SureSelect exome pull down kits, and the like. As shown in FIG. 1, application of a targeted enrichment results in enriched, barcoded sequence library 118. Further, because the pulled down fragments within library 118 retain their original molecular context, e.g., through the retention of the barcode information, they may be reassembled into their original molecular contexts with embedded long range linkage information, e.g., with inferred linkage as between each of the assembled regions of interest 106:108 and 110:112. By way of example, one may identify direct molecular linkage between two disparate targeted portions of the genome, e.g., two or more exons, and that direct molecular linkage may be used to identify structural variations and other genomic characteristics, as well as to identify the phase information as to the two or more exons, e.g. providing phased exons, including potentially an entire phased exome, or other phased targeted portions of a genome.

Figure 7:
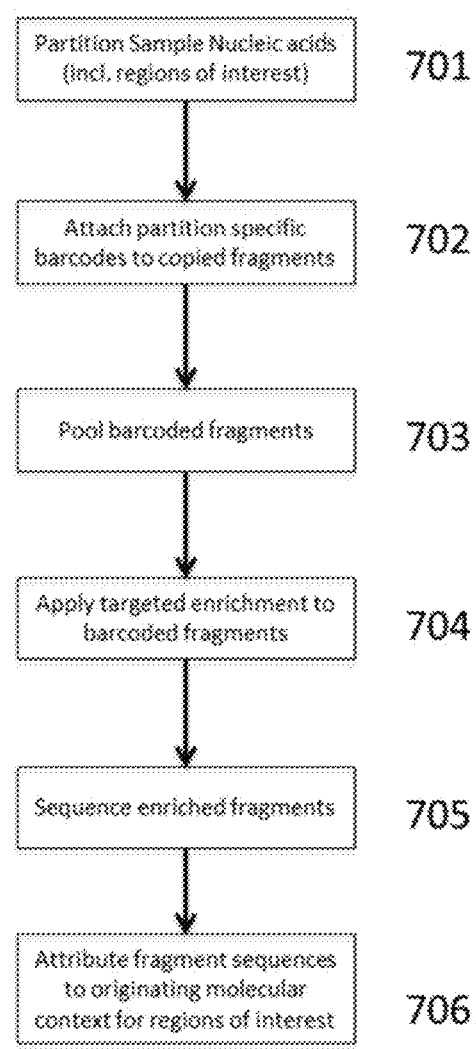
FIG. 7 illustrates a general embodiment of a method of the invention.

Generally, methods of the invention include steps as illustrated in FIG. 7, which provides a schematic overview of methods of the invention discussed in further detail herein. As will be appreciated, the method outlined in FIG. 9 is an exemplary embodiment that may be altered or modified as needed and as described herein.

As shown in FIG. 7, the methods described herein will in most examples include a step in which sample nucleic acids containing the targeted regions of interest are partitioned (701). Generally, each partition will include a single individual nucleic acid molecule from a particular locus that is then fragmented or copied in such a way as to preserve the original molecular context of the fragments (702), usually by barcoding the fragments that are specific to the partition in which they are contained. Each partition may in some examples include more than one nucleic acid, and will in some instances contain several hundred nucleic acid molecules—in situations in which multiple nucleic acids are within a partition, any particular locus of the genome will generally be represented by a single individual nucleic acid prior to barcoding. The barcoded fragments of step 702 can be generated using any methods known in the art—in some examples, oligonucleotides are the samples within the distinct partitions. Such oligonucleotides may comprise random sequences intended to randomly prime numerous different regions of the samples, or they may comprise a specific primer sequence targeted to prime upstream of a targeted region of the sample. In further examples, these oligonucleotides also contain a barcode sequence, such that the replication process also barcodes the resultant replicated fragment of the original sample nucleic acid. A particularly elegant process for use of these barcode oligonucleotides in amplifying and barcoding samples is described in detail in U.S. patent application Ser. Nos. 14/316,383, 14/316,398, 14/316,416, 14/316,431, 14/316,447, 14/316,463, all filed Jun. 26, 2014, each of which is herein incorporated by reference in its entirety for all purposes. Extension reaction reagents, e.g., DNA polymerase, nucleoside triphosphates, co-factors (e.g., $Mg^{2+}$ or $Mn^{2+}$ etc.), that are also contained in the partitions, then extend the primer sequence using the sample as a template, to produce a complementary fragment to the strand of the template to which the primer annealed, and the complementary fragment includes the oligonucleotide and its associated barcode sequence. Annealing and extension of multiple primers to different portions of the sample can result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In further examples, this replication process is configured such that when the first complement is duplicated, it produces two complementary sequences at or near its termini to allow the formation of a hairpin structure or partial hairpin structure, which reduces the ability of the molecule to be the basis for producing further iterative copies.

Returning to the method exemplified in FIG. 7, once the partition-specific barcodes are attached to the copied fragments, the barcoded fragments are then pooled (703). Target enrichment techniques can then be applied (704) to "pull down" the targeted regions of interest. Those targeted regions of interest are then sequenced (705) and the sequences of the fragments are attributed to their originating molecular context (706), such that the targeted regions of interest are both identified and also linked with that originating molecular context. A unique feature of the methods and systems described herein and illustrated in FIG. 7 is that barcodes are attached to the fragments (702) prior to the targeted enrichment step (704). An advantage of the methods and systems described herein is that attaching a partition- or sample-specific barcode to the copied fragments prior to enriching the fragments for targeted genomic regions preserves the original molecular context of those targeted regions, allowing them to be attributed to their original partition and thus their originating sample nucleic acid.

In general, targeted genomic regions are enriched, isolated or separated, i.e., "pulled down," for further analysis, particularly sequencing, using methods that include both chip-based and solution-based capture methods. Such methods utilize probes that are complementary to the genomic regions of interest or to regions near or adjacent to the genomic regions of interest. For example, in hybrid (or chip-based) capture, microarrays containing capture probes (usually single-stranded oligonucleotides) with sequences that taken together cover the region of interest are fixed to a surface. Genomic DNA is fragmented and may further undergo processing such as end-repair to produce blunt ends and/or addition of additional features such as universal priming sequences. These fragments are hybridized to the probes on the microarray. Unhybridized fragments are washed away and the desired fragments are eluted or otherwise processed on the surface for sequencing or other analysis, and thus the population of fragments remaining on the surface is enriched for fragments containing the targeted regions of interest (e.g., the regions comprising the sequences complementary to those contained in the capture probes). The enriched population of fragments may further be amplified using any amplification technologies known in the art.

Additional methods of targeted genomic region capture include solution-based methods, in which genomic DNA fragments are hybridized to oligonucleotide probes. The oligonucleotide probes are often referred to as "baits". These baits are generally attached to a capture molecule, including without limitation a biotin molecule. The baits are complementary to targeted regions of the genome (or to regions near or adjacent to the targeted regions of interest), such that upon application to genomic DNA fragments, the baits hybridize to the fragments, and the capture molecule (e.g., biotin) is then used to selectively pull down the targeted regions of interest (for example, with magnetic streptavidin beads) to thereby enrich the resultant population of fragments with those containing the targeted regions of interest.

In examples in which targeted regions covering the whole exome are needed, a library of baits that together cover the whole exome is used to capture those targeted sequences. In such examples, capture protocols can include any of those known in the art, including without limitation any of the exome capture protocols and kits produced by Roche/ NimbleGen, Illumina, and Agilent.

Capture of targeted genomic regions for use in the methods and systems described herein are not limited to whole exomes, and can include any one or combination of partial exomes, genes, panels of genes, introns, and combinations of introns and exons. The procedure for capture of these different types of targeted regions follows the general method of using baits to pull down fragments containing the targeted regions of interest. The design of the baits, particularly the oligonucleotide probe portions of the baits that hybridize to or near to the targeted regions of interest, will in part depend on the type of targeted region to be captured.

In examples in which only a partial exome is needed for further analysis, the baits can be designed to capture that part of the exome. In certain examples, the specific identities of the portions of the exome that are needed are known, and the library of baits comprises oligonucleotides that are complementary to those identified portions or to regions that are near or adjacent to those portions. Such examples can further include without limitation capture of specific genes and/or panels of genes, or identified portions of the exome known to be associated with a particular phenotype, such as a disorder or disease. In some examples, it may be that a certain portion of the exome or the whole genome (including both intronic and exonic regions) is needed for further analysis, but the specific sequences for the portions of the genome to be captured are not known. In such embodiments, the baits used can be subsets of a library directed to a whole genome, and that subset can be chosen randomly or through any kind of intelligent design in which the library of baits is selected or enriched for probes that are complementary to the targeted subsections of the genome or exome.

Figure 2A:
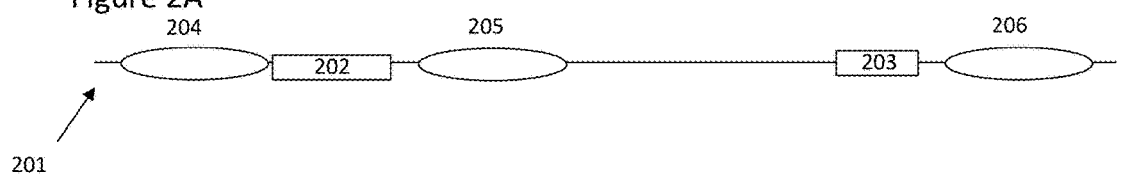
FIG. 2A and FIG. 2B provide schematic illustrations of identification and analysis of targeted genomic regions using processes and systems described herein.

For any of the methods described herein, the targeted regions can be captured using baits that comprise oligonucleotide probes that are complementary to the whole or part of a targeted region, or the oligonucleotide probes may be complementary to another region, e.g., an intronic region, that is near the targeted region or adjacent to the targeted region. For example, as schematically illustrated in FIG. 2A, a genomic sequence 201 comprises exonic regions 202 and 203. Those exonic regions can be captured by directing the baits to one or more of the intronic sequences nearby (for example intronic region 204 and/or 205 to capture exonic region 202 and intronic region 206 for capture of exonic region 203). In other words, a population of fragments comprising exonic regions 202 or 203 can be captured through the use of baits complementary to intronic regions 204 and/or 205 and 206. As shown in FIG. 2A, the intronic region used as an intronic bait for the nearby exonic region can be adjacent to the exonic region of interest—i.e., there is no gap between the intronic region and the targeted exonic region. In other examples, the intronic region used to capture the nearby exonic region may be near enough so that both regions are likely to be in the same fragment, but there is a gap of one or more nucleotides between the exonic region and the intronic region (for example 202 and 205 in FIG. 2A).

In some examples, rather than designing the baits to target particular regions of the genome, a tiling approach is used. In such an approach, rather than targeting specific exonic or intronic regions, the baits are designed to be complementary to portions of the genome at particular ranges or distances. For example, the library of baits can be designed to cover sequences every 5 kilobases (kb) along the genome, such that applying this library of baits to a fragmented genomic sample will capture only a certain subset of the genome—i.e., those regions that are contained in fragments containing complementary sequences to the baits. As will be appreciated, the baits can be designed based on a reference sequence, such as a human genome reference sequence. In further examples, the tiled library of baits is designed to capture regions every 1, 2, 5, 10, 15, 20, 25, 50, 100, 200, 250, 500, 750, 1000, or 10000 kilobases of a genome. In still further examples, the tiled library of baits is designed to capture a mixture of distances—that mixture can be a random mixture of distances or intelligently designed such that a specific portion or percentage of the genome is captured. As will be appreciated, such tiling methods of capture will capture both intronic and exonic regions of the genome for further analysis such as sequencing. Any of the tiling or other intronic baiting methods described herein provide a way to link sequence information from exons widely separated by long intervening intronic regions.

In further examples, the tiling or other capture methods described herein will capture about 5%, 10%, 15%, 20%, 30%, 40%, 50%, 60%, 70%, 80%, 90%, 95% of the whole genome. In still further examples, the capture methods described herein capture about 1-10%, 5-20%, 10-30%, 15-40%, 20-50%, 25-60%, 30-70%, 35-80%, 40-90%, or 45-95% of the whole genome.

Figure 2B:
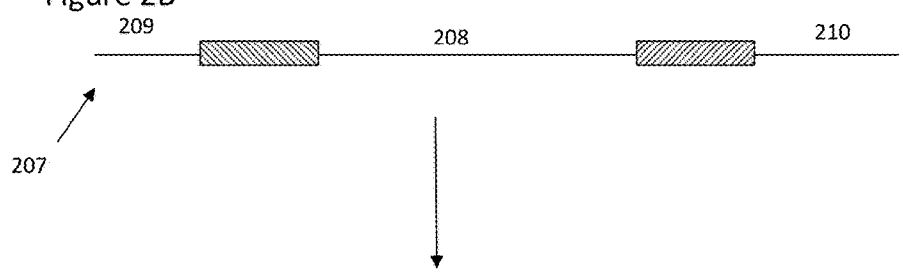
Figure 2B:
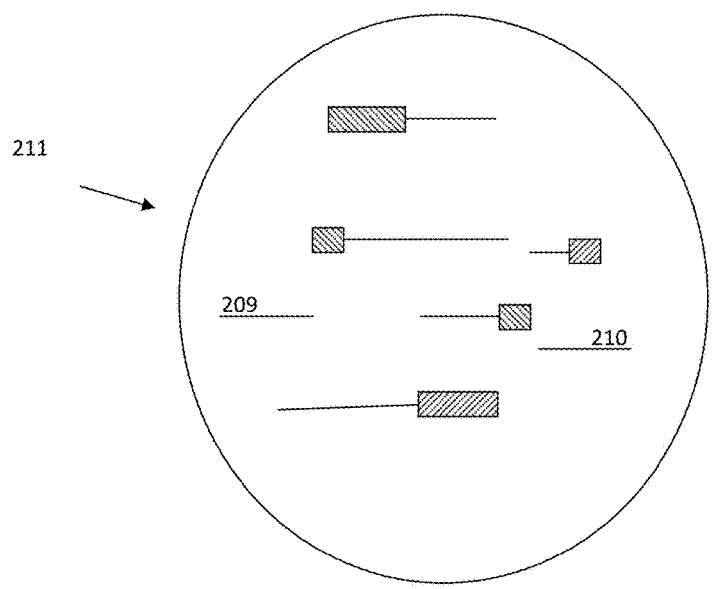

In some examples, sample preparation methods, including methods of fragmenting, amplifying, partitioning, and otherwise processing genomic DNA, can lead to biases or lower coverage of certain regions of a genome. Such biases or lowered coverage can be compensated for in the methods and systems disclosed herein by altering the concentration or genomic locations of baits used to capture targeted regions of the genome. In some examples, it may be known that certain regions of the genome containing high GC content or other structural variations will lead to low coverage—in such situations, the library of baits can be altered to increase the concentration of baits directed to those regions of low coverage—in other words, the population of baits used may be "spiked" to ensure that a sufficient number of fragments containing targeted regions of the genome in those low coverage areas are obtained in the final population of fragments to be sequenced. Such spiking of baits may be conducted in commercially available whole exome kits, such that a custom library of baits directed toward the lower coverage regions are added to off-the-shelf exome capture kits. Additionally, baits can be design to target a region of the genome that is very close to the region of interest, but has more favorable coverage, as is also discussed in further detail herein and embodiments of which are schematically illustrated in FIG. 2.

In further examples, the library of baits used in methods of the present invention is a product of informed design that fulfills one or more characteristics as further described herein. This informed design includes instances in which the library of baits is directed to informative single nucleotide polymorphisms (SNPs). The term "informative SNPs" as used herein refers to SNPs that are heterozygous. The library of baits in some examples is designed to contain a plurality of probes that are directed to regions of the genomic sample that contain informative SNPs. By "directed to" as used herein is meant that the probes contain sequences that are complementary to sequences that encompass the SNPs. In further examples, the library of baits is designed to contain probes directed to SNPs that are at predetermined distances from the boundary of an exon and an intron. In situations in which the targeted regions of the genome include regions that are devoid of or contain very few SNPs, the library of baits includes probes that tile across such regions at a predetermined distance and/or that hybridize to the first informative SNP within the next nearest intron or exon.

An advantage of the methods and systems described herein is that the targeted regions that are captured are processed prior to capture in such a way that even after the steps of capturing the targeted regions and conducting sequencing analyses, the original molecular context of those targeted regions is retained. As is discussed in further detail herein, the ability to attribute specific targeted regions to their original molecular context (which can include the original chromosome or chromosomal region from which they are derived and/or the location of particular targeted regions in relation to each other within the full genome) provides a way to obtain sequence information from regions of the genome that are otherwise poorly mapped or have poor coverage using traditional sequencing techniques.

For example, some genes possess long introns that are too long to span using generally available sequencing techniques, particularly using short-read technologies that possess superior accuracy as compared to long-read technologies. In the methods and systems described herein, however, the molecular context of targeted regions is retained, generally through the tagging procedure illustrated in FIG. 1 and described in further detail herein. As such, links can be made across extended regions of the genome. For example, as schematically illustrated in FIG. 2B, nucleic acid molecule 207 contains two exons (shaded bars) interrupted by a long intronic region (208). Generally used sequencing technologies would be unable to span the distance across the intron to provide information on the relationship of the two exons. In the methods described herein, the individual nucleic acid molecule 207 is distributed into its own discrete partition 209 and then fragmented such that different fragments contain different portions of the exons and the intron. Because each of those fragments is tagged such that any sequence information obtained from the fragments is then attributable to the discrete partition in which it was generated, each fragment is thus also attributable to the individual nucleic acid molecule 207 from which it was derived. In general, and as is described in further detail herein, after fragmentation and tagging, fragments from different partitions are combined together. Targeted capture methods can then be used to enrich the population of fragments that undergoes further analysis, such as sequencing, with fragments containing the targeted region of interest. In the example illustrated in FIG. 2B, the baits used will enrich the population of fragments to capture only those containing a portion of one of the two exons and/or part of the intervening intron, but regions outside of the exons and intron (such as 209 and 210) would not be captured. Thus, the final population of fragments that undergoes sequencing will be enriched for the fragments containing portions of the two exons of interest. Short read, high accuracy sequencing technologies can then be used to identify the sequences of this enriched population of fragments, and because each of the fragments is tagged and thus attributable to its original molecular context, i.e., its original individual nucleic acid molecule, the short read sequences can provide information that spans over the long length of the intervening intron to provide information on the relationship between the two exons.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. As will be appreciated, by providing long range individual molecular context, one can also derive the phasing information of variants within that individual molecular context, e.g., variants on a particular long molecule will be, by definition commonly phased.

By providing longer range individual molecular context, the methods and systems of the invention also provide much longer inferred molecular context (also referred to herein as a "long virtual single molecule read"). Sequence context, as described herein can include mapping or providing linkage of fragments across different (generally on the kilobase scale) ranges of full genomic sequence. These methods include mapping the short sequence reads to the individual longer molecules or contigs of linked molecules, as well as long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

Furthermore, while one may utilize the long range sequence context associated with long individual molecules, having such long range sequence context also allows one to infer even longer range sequence context. By way of one example, by providing the long range molecular context described above, one can identify overlapping variant portions, e.g., phased variants, translocated sequences, etc., among long sequences from different originating molecules, allowing the inferred linkage between those molecules. Such inferred linkages or molecular contexts are referred to herein as "inferred contigs". In some cases when discussed in the context of phased sequences, the inferred contigs may represent commonly phased sequences, e.g., where by virtue of overlapping phased variants, one can infer a phased contig of substantially greater length than the individual originating molecules. These phased contigs are referred to herein as "phase blocks".

By starting with longer single molecule reads (e.g., the "long virtual single molecule reads" discussed above), one can derive longer inferred contigs or phase blocks than would otherwise be attainable using short read sequencing technologies or other approaches to phased sequencing. See, e.g., published U.S. Patent Application No. 2013-0157870. In particular, using the methods and systems described herein, one can obtain inferred contig or phase block lengths having an N50 (where the sum of the block lengths that are greater than the stated N50 number is 50% of the sum of all block lengths) of at least about 10 kb, at least about 20 kb, at least about 50 kb. In more preferred aspects, inferred contig or phase block lengths having an N50 of at least about 100 kb, at least about 150 kb, at least about 200 kb, and in many cases, at least about 250 kb, at least about 300 kb, at least about 350 kb, at least about 400 kb, and in some cases, at least about 500 kb or more, are attained. In still other cases, maximum phase block lengths in excess of 200 kb, in excess of 300 kb, in excess of 400 kb, in excess of 500 kb, in excess of 1 Mb, or even in excess of 2 Mb may be obtained.

In one aspect, and in conjunction with any of the capture methods described above and later herein, the methods and systems described herein provide for the compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned sample nucleic acids, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

The sample nucleic acids utilized in the methods described herein typically represent a number of overlapping portions of the overall sample to be analyzed, e.g., an entire chromosome, exome, or other large genomic portion. These sample nucleic acids may include whole genomes, individual chromosomes, exomes, amplicons, or any of a variety of different nucleic acids of interest. The sample nucleic acids are typically partitioned such that the nucleic acids are present in the partitions in relatively long fragments or stretches of contiguous nucleic acid molecules. Typically, these fragments of the sample nucleic acids may be longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range molecular context described above.

The sample nucleic acids are also typically partitioned at a level whereby a given partition has a very low probability of including two overlapping fragments of the starting sample nucleic acid. This is typically accomplished by providing the sample nucleic acid at a low input amount and/or concentration during the partitioning process. As a result, in preferred cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Published Application No. 2013-0079231 and 2013-0157870) typically only operate with a hundred to a few hundred different barcode sequences, and employ a limiting dilution process of their sample in order to be able to attribute barcodes to different cells/nucleic acids. As such, they will generally operate with far fewer than 100 cells, which would typically provide a ratio of genomes:(barcode type) on the order of 1:10, and certainly well above 1:100. The systems described herein, on the other hand, because of the high level of barcode diversity, e.g., in excess of 10,000, 100,000, 500,000, etc. diverse barcode types, can operate at genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

Often, the sample is combined with a set of oligonucleotide tags that are releasably-attached to beads prior to the partitioning step. That combination can then lead to barcoding of nucleic acids in the samples using methods known in the art and described herein. In some examples, amplification methods are used to add barcodes to the resultant amplification products, which in some examples contain smaller segments (fragments) of the full originating nucleic acid molecule from which they are derived. In some examples, methods using transposons are utilized as described in Amini et al, Nature Genetics 46: 1343-1349 (2014) (advance online publication on Oct. 29, 2014), which is herein incorporated by reference in its entirety for all purposes and in particular for all teachings related to attaching barcodes or other oligonucleotide tags to nucleic acids. In further examples, methods of attaching barcodes can include the use of nicking enzymes or polymerases and/or invasive probes such as recA to produce gaps along double stranded sample nucleic acids—barcodes can then be inserted into those gaps.

In examples in which amplification is used to tag nucleic acid fragments, the oligonucleotide tags may comprise at least a first and second region. The first region may be a barcode region that, as between oligonucleotides within a given partition, may be substantially the same barcode sequence, but as between different partitions, may and, in most cases is a different barcode sequence. The second region may be an N-mer (either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, e.g., an exome or other targeted region. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn, as can analyses across long ranges of genomic sequence—for example, identification of sequence information across stretches of poorly characterized regions of the genome. Such information may also be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Ensemble sample preparation and sequencing methods are predisposed towards primarily identifying and characterizing the majority constituents in the sample, and are not designed to identify and characterize minority constituents, e.g., genetic material contributed by one chromosome, or by one or a few cells, or fragmented tumor cell DNA molecule circulating in the bloodstream, that constitute a small percentage of the total DNA in the extracted sample. The described methods and systems also provide a significant advantage for detecting populations that are present within a larger sample. As such, they are particularly useful for assessing haplotype and copy number variations—the methods disclosed herein are also useful for providing sequence information over regions of the genome that are poorly characterized or are poorly represented in a population of nucleic acid targets due to biases introduced during sample preparation.

The use of the barcoding technique disclosed herein confers the unique capability of providing individual molecular context for a given set of genetic markers, i.e., attributing a given set of genetic markers (as opposed to a single marker) to individual sample nucleic acid molecules, and through variant coordinated assembly, to provide a broader or even longer range inferred individual molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

As described previously, an advantage of the methods and systems described herein is that they can achieve the desired results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, inc. (GXII, NextSeq, MiSeq, HiSeq, X10), Ion Torrent division of Thermo-Fisher (Ion Proton and Ion PGM), pyrosequencing methods, as well as others.

Of particular advantage is that the methods and systems described herein utilize these short read sequencing technologies and do so with their associated low error rates. In particular, the methods and systems described herein achieve the desired individual molecular readlengths or context, as described above, but with individual sequencing reads, excluding mate pair extensions, that are shorter than 1000 bp, shorter than 500 bp, shorter than 300 bp, shorter than 200 bp, shorter than 150 bp or even shorter; and with sequencing error rates for such individual molecular readlengths that are less than 5%, less than 1%, less than 0.5%, less than 0.1%, less than 0.05%, less than 0.01%, less than 0.005%, or even less than 0.001%.

II. Work Flow Overview

In one exemplary aspect, the methods and systems described in the disclosure provide for depositing or partitioning individual samples (e.g., nucleic acids) into discrete partitions, where each partition maintains separation of its own contents from the contents in other partitions. As used herein, the partitions refer to containers or vessels that may include a variety of different forms, e.g., wells, tubes, micro or nanowells, through holes, or the like. In preferred aspects, however, the partitions are flowable within fluid streams. These vessels may be comprised of, e.g., microcapsules or micro-vesicles that have an outer barrier surrounding an inner fluid center or core, or they may be a porous matrix that is capable of entraining and/or retaining materials within its matrix. In preferred aspect, however, these partitions may comprise droplets of aqueous fluid within a non-aqueous continuous phase, e.g., an oil phase. A variety of different vessels are described in, for example, U.S. patent application Ser. No. 13/966,150, filed Aug. 13, 2013. Likewise, emulsion systems for creating stable droplets in non-aqueous or oil continuous phases are described in detail in, e.g., Published U.S. Patent Application No. 2010-0105112. In certain cases, microfluidic channel networks are particularly suited for generating partitions as described herein. Examples of such microfluidic devices include those described in detail in U.S. patent application Ser. No. 14/682,952, filed Apr. 9, 2015, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of sample materials, e.g., nucleic acids, into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides. The relative amount of sample materials within any particular partition may be adjusted by controlling a variety of different parameters of the system, including, for example, the concentration of sample in the aqueous stream, the flow rate of the aqueous stream and/or the non-aqueous stream, and the like. The partitions described herein are often characterized by having extremely small volumes. For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes. In some cases, the use of low reaction volume partitions is particularly advantageous in performing reactions with very small amounts of starting reagents, e.g., input nucleic acids. Methods and systems for analyzing samples with low input nucleic acids are presented in U.S. patent application Ser. No. 14/752,602, filed Jun. 26, 2015, the full disclosure of which is hereby incorporated by reference in its entirety.

Once the samples are introduced into their respective partitions, in accordance with the methods and systems described herein, the sample nucleic acids within partitions are generally provided with unique identifiers such that, upon characterization of those nucleic acids they may be attributed as having been derived from their respective origins. Accordingly, the sample nucleic acids are typically co-partitioned with the unique identifiers (e.g., barcode sequences). In particularly preferred aspects, the unique identifiers are provided in the form of oligonucleotides that comprise nucleic acid barcode sequences that may be attached to those samples. The oligonucleotides are partitioned such that as between oligonucleotides in a given partition, the nucleic acid barcode sequences contained therein are the same, but as between different partitions, the oligonucleotides can, and preferably have differing barcode sequences. In preferred aspects, only one nucleic acid barcode sequence will be associated with a given partition, although in some cases, two or more different barcode sequences may be present.

The nucleic acid barcode sequences will typically include from 6 to about 20 or more nucleotides within the sequence of the oligonucleotides. These nucleotides may be completely contiguous, i.e., in a single stretch of adjacent nucleotides, or they may be separated into two or more separate subsequences that are separated by one or more nucleotides. Typically, separated subsequences may typically be from about 4 to about 16 nucleotides in length.

The co-partitioned oligonucleotides also typically comprise other functional sequences useful in the processing of the partitioned nucleic acids. These sequences include, e.g., targeted or random/universal amplification primer sequences for amplifying the genomic DNA from the individual nucleic acids within the partitions while attaching the associated barcode sequences, sequencing primers, hybridization or probing sequences, e.g., for identification of presence of the sequences, or for pulling down barcoded nucleic acids, or any of a number of other potential functional sequences. Again, co-partitioning of oligonucleotides and associated barcodes and other functional sequences, along with sample materials is described in, for example, U.S. patent application Ser. Nos. 14/316,383, 14/316,398, 14/316,416, 14/316,431, 14/316,447, 14/316,463, all filed Jun. 26, 2014, as well as U.S. patent application Ser. No. 14/175,935, filed Feb. 7, 2014, the full disclosures of which is hereby incorporated by reference in their entireties.

Briefly, in one exemplary process, beads are provided that each may include large numbers of the above described oligonucleotides releasably attached to the beads, where all of the oligonucleotides attached to a particular bead may include the same nucleic acid barcode sequence, but where a large number of diverse barcode sequences may be represented across the population of beads used. Typically, the population of beads may provide a diverse barcode sequence library that may include at least 1000 different barcode sequences, at least 10,000 different barcode sequences, at least 100,000 different barcode sequences, or in some cases, at least 1,000,000 different barcode sequences. Additionally, each bead may typically be provided with large numbers of oligonucleotide molecules attached. In particular, the number of molecules of oligonucleotides including the barcode sequence on an individual bead may be at least bout 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

The oligonucleotides may be releasable from the beads upon the application of a particular stimulus to the beads. In some cases, the stimulus may be a photo-stimulus, e.g., through cleavage of a photo-labile linkage that may release the oligonucleotides. In some cases, a thermal stimulus may be used, where elevation of the temperature of the beads environment may result in cleavage of a linkage or other release of the oligonucleotides form the beads. In some cases, a chemical stimulus may be used that cleaves a linkage of the oligonucleotides to the beads, or otherwise may result in release of the oligonucleotides from the beads.

In accordance with the methods and systems described herein, the beads including the attached oligonucleotides may be co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 3:
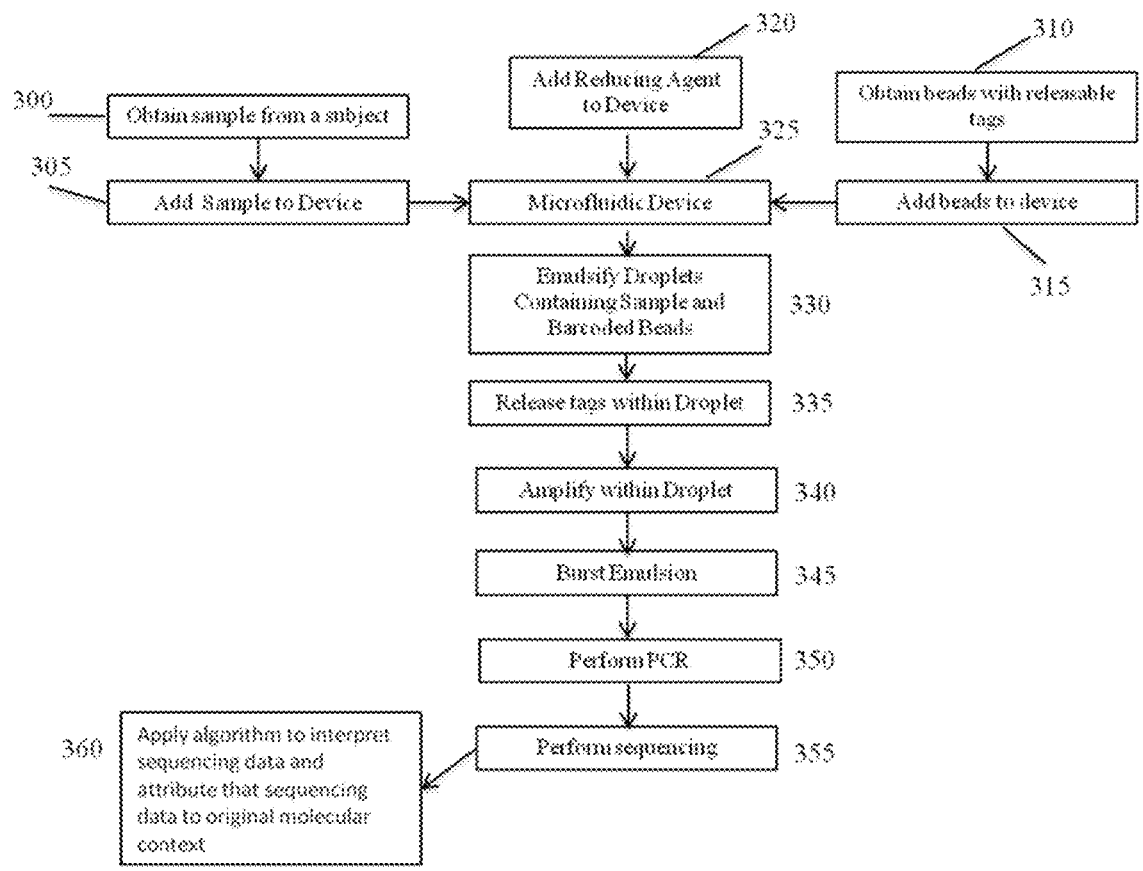
FIG. 3 illustrates a typical workflow for performing an assay to detect sequence information, using the methods and compositions disclosed herein.

FIG. 3 illustrates one particular example method for barcoding and subsequently sequencing a sample nucleic acid, particularly for use for a copy number variation or haplotype assay. First, a sample comprising nucleic acid may be obtained from a source, 300, and a set of barcoded beads may also be obtained, 310. The beads are preferably linked to oligonucleotides containing one or more barcode sequences, as well as a primer, such as a random N-mer or other primer. Preferably, the barcode sequences are releasable from the barcoded beads, e.g., through cleavage of a linkage between the barcode and the bead or through degradation of the underlying bead to release the barcode, or a combination of the two. For example, in certain preferred aspects, the barcoded beads can be degraded or dissolved by an agent, such as a reducing agent to release the barcode sequences. In this example, a low quantity of the sample comprising nucleic acid, 305, barcoded beads, 315, and optionally other reagents, e.g., a reducing agent, 320, are combined and subject to partitioning. By way of example, such partitioning may involve introducing the components to a droplet generation system, such as a microfluidic device, 325. With the aid of the microfluidic device 325, a water-in-oil emulsion 330 may be formed, wherein the emulsion contains aqueous droplets that contain sample nucleic acid, 305, reducing agent, 320, and barcoded beads, 315. The reducing agent may dissolve or degrade the barcoded beads, thereby releasing the oligonucleotides with the barcodes and random N-mers from the beads within the droplets, 335. The random N-mers may then prime different regions of the sample nucleic acid, resulting in amplified copies of the sample after amplification, wherein each copy is tagged with a barcode sequence, 340. Preferably, each droplet contains a set of oligonucleotides that contain identical barcode sequences and different random N-mer sequences. Subsequently, the emulsion is broken, 345 and additional sequences (e.g., sequences that aid in particular sequencing methods, additional barcodes, etc.) may be added, via, for example, amplification methods, 350 (e.g., PCR). Sequencing may then be performed, 355, and an algorithm applied to interpret the sequencing data, 360. Sequencing algorithms are generally capable, for example, of performing analysis of barcodes to align sequencing reads and/or identify the sample from which a particular sequence read belongs. In addition, and as is described herein, these algorithms may also further be used to attribute the sequences of the copies to their originating molecular context.

Figure 4:
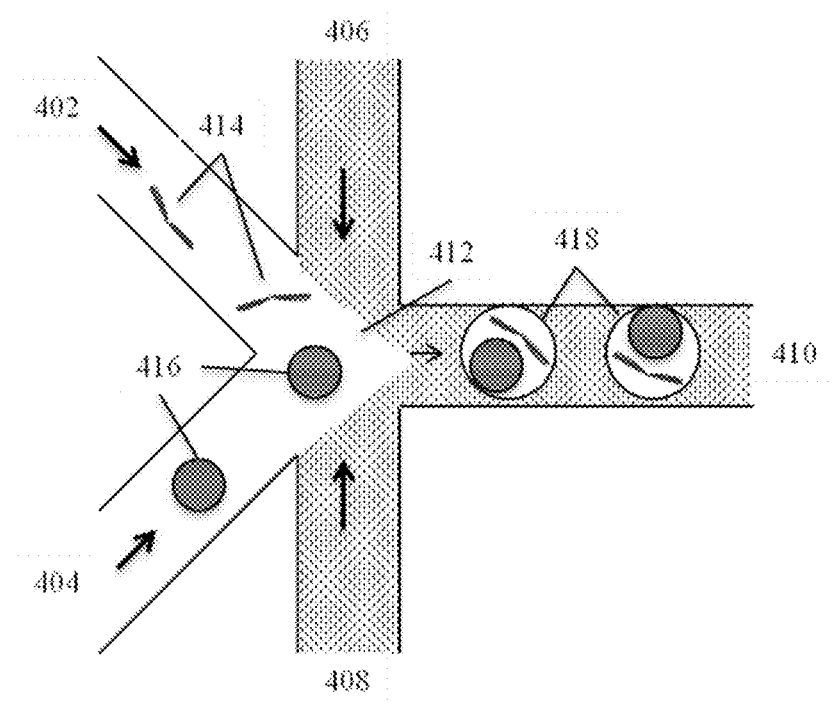
FIG. 4 provides a schematic illustration of a process for combining a nucleic acid sample with beads and partitioning the nucleic acids and beads into discrete droplets.

As noted above, while single bead occupancy may be the most desired state, it will be appreciated that multiply occupied partitions or unoccupied partitions may often be present. An example of a microfluidic channel structure for co-partitioning samples and beads comprising barcode oligonucleotides is schematically illustrated in FIG. 4. As shown, channel segments 402, 404, 406, 408 and 410 are provided in fluid communication at channel junction 412. An aqueous stream comprising the individual samples 414 is flowed through channel segment 402 toward channel junction 412. As described elsewhere herein, these samples may be suspended within an aqueous fluid prior to the partitioning process.

Concurrently, an aqueous stream comprising the barcode carrying beads 416 is flowed through channel segment 404 toward channel junction 412. A non-aqueous partitioning fluid is introduced into channel junction 412 from each of side channels 406 and 408, and the combined streams are flowed into outlet channel 410. Within channel junction 412, the two combined aqueous streams from channel segments 402 and 404 are combined, and partitioned into droplets 418, that include co-partitioned samples 414 and beads 416. As noted previously, by controlling the flow characteristics of each of the fluids combining at channel junction 412, as well as controlling the geometry of the channel junction, one can optimize the combination and partitioning to achieve a desired occupancy level of beads, samples or both, within the partitions 418 that are generated.

As will be appreciated, a number of other reagents may be co-partitioned along with the samples and beads, including, for example, chemical stimuli, nucleic acid extension, transcription, and/or amplification reagents such as polymerases, reverse transcriptases, nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

Once co-partitioned, the oligonucleotides disposed upon the bead may be used to barcode and amplify the partitioned samples. A particularly elegant process for use of these barcode oligonucleotides in amplifying and barcoding samples is described in detail in U.S. patent application Ser. Nos. 14/316,383, 14/316,398, 14/316,416, 14/316,431, 14/316,447, 14/316,463, all filed Jun. 26, 2014, the full disclosures of which are hereby incorporated by reference in their entireties. Briefly, in one aspect, the oligonucleotides present on the beads that are co-partitioned with the samples and released from their beads into the partition with the samples. The oligonucleotides typically include, along with the barcode sequence, a primer sequence at its 5' end. This primer sequence may be random or structured. Random primer sequences are generally intended to randomly prime numerous different regions of the samples. Structured primer sequences can include a range of different structures including defined sequences targeted to prime upstream of a specific targeted region of the sample as well as primers that have some sort of partially defined structure, including without limitation primers containing a percentage of specific bases (such as a percentage of GC N-mers), primers containing partially or wholly degenerate sequences, and/or primers containing sequences that are partially random and partially structured in accordance with any of the description herein. As will be appreciated, any one or more of the above types of random and structured primers may be included in oligonucleotides in any combination.

Figure 5:
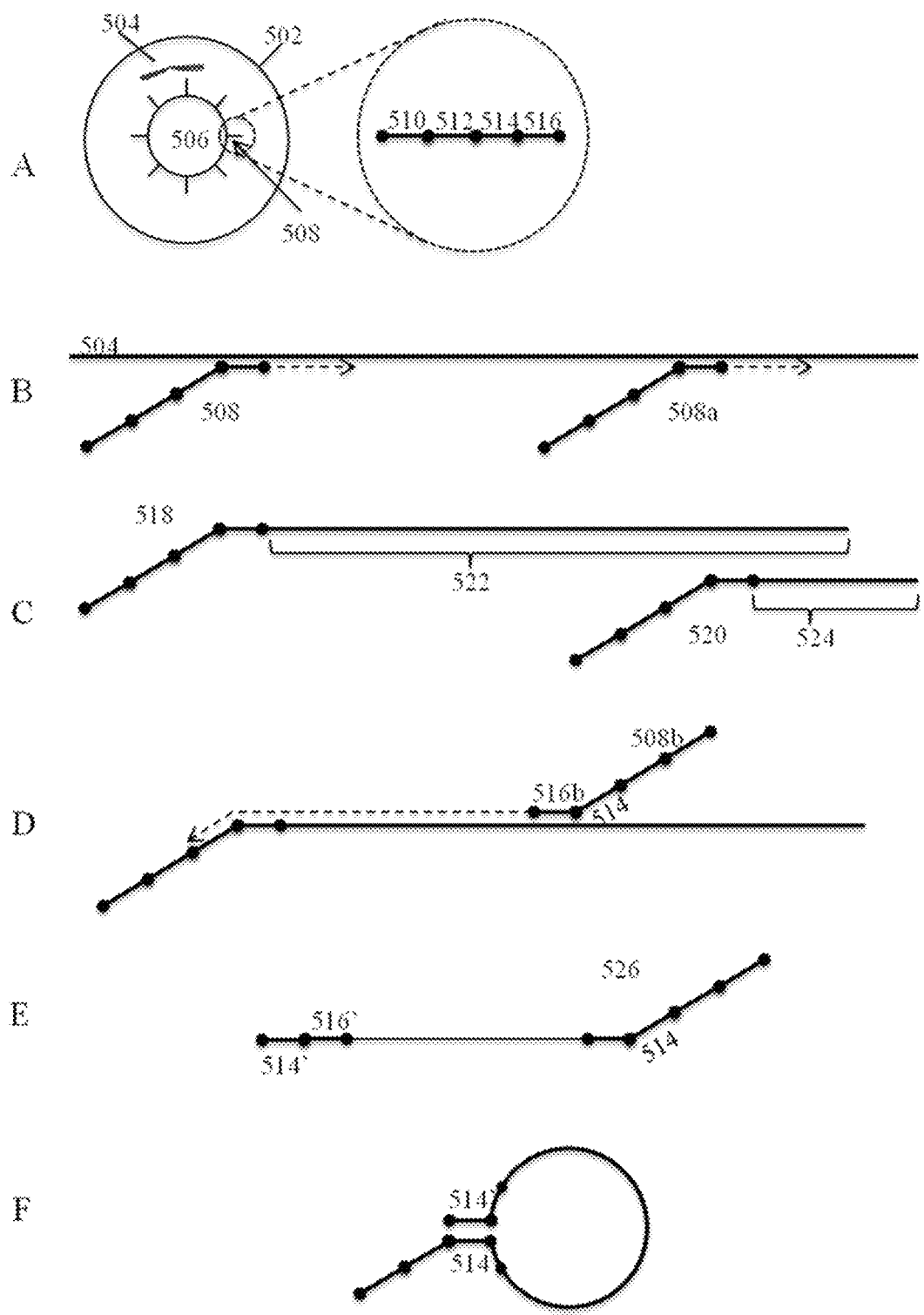
FIG. 5 provides a schematic illustration of a process for barcoding and amplification of chromosomal nucleic acid fragments.

Once released, the primer portion of the oligonucleotide can anneal to a complementary region of the sample. Extension reaction reagents, e.g., DNA polymerase, nucleoside triphosphates, co-factors (e.g., Mg2+ or Mn2+ etc.), that are also co-partitioned with the samples and beads, then extend the primer sequence using the sample as a template, to produce a complementary fragment to the strand of the template to which the primer annealed, with complementary fragment includes the oligonucleotide and its associated barcode sequence. Annealing and extension of multiple primers to different portions of the sample may result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure, which reduces the ability of the molecule to be the basis for producing further iterative copies. A schematic illustration of one example of this is shown in FIG. 5.

As the figure shows, oligonucleotides that include a barcode sequence are co-partitioned in, e.g., a droplet 502 in an emulsion, along with a sample nucleic acid 504. As noted elsewhere herein, the oligonucleotides 508 may be provided on a bead 506 that is co-partitioned with the sample nucleic acid 504, which oligonucleotides are preferably releasable from the bead 506, as shown in panel A. The oligonucleotides 508 include a barcode sequence 512, in addition to one or more functional sequences, e.g., sequences 510, 514 and 516. For example, oligonucleotide 508 is shown as comprising barcode sequence 512, as well as sequence 510 that may function as an attachment or immobilization sequence for a given sequencing system, e.g., a P5 sequence used for attachment in flow cells of an Illumina Hiseq or Miseq system. As shown, the oligonucleotides also include a primer sequence 516, which may include a random or targeted N-mer for priming replication of portions of the sample nucleic acid 504. Also included within oligonucleotide 508 is a sequence 514 which may provide a sequencing priming region, such as a "read1" or R1 priming region, that is used to prime polymerase mediated, template directed sequencing by synthesis reactions in sequencing systems. In many cases, the barcode sequence 512, immobilization sequence 510 and R1 sequence 514 may be common to all of the oligonucleotides attached to a given bead. The primer sequence 516 may vary for random N-mer primers, or may be common to the oligonucleotides on a given bead for certain targeted applications.

Based upon the presence of primer sequence 516, the oligonucleotides are able to prime the sample nucleic acid as shown in panel B, which allows for extension of the oligonucleotides 508 and 508a using polymerase enzymes and other extension reagents also co-portioned with the bead 506 and sample nucleic acid 504. As shown in panel C, following extension of the oligonucleotides that, for random N-mer primers, would anneal to multiple different regions of the sample nucleic acid 504; multiple overlapping complements or fragments of the nucleic acid are created, e.g., fragments 518 and 520. Although including sequence portions that are complementary to portions of sample nucleic acid, e.g., sequences 522 and 524, these constructs are generally referred to herein as comprising fragments of the sample nucleic acid 504, having the attached barcode sequences. As will be appreciated, the replicated portions of the template sequences as described above are often referred to herein as "fragments" of that template sequence. Notwithstanding the foregoing, however, the term "fragment" encompasses any representation of a portion of the originating nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In preferred aspects, however, fragments of a template or sample nucleic acid sequence will denote replicated portions of the underlying sequence or complements thereof.

The barcoded nucleic acid fragments may then be subjected to characterization, e.g., through sequence analysis, or they may be further amplified in the process, as shown in panel D. For example, additional oligonucleotides, e.g., oligonucleotide 508b, also released from bead 306, may prime the fragments 518 and 520. In particular, again, based upon the presence of the random N-mer primer 516b in oligonucleotide 508b (which in many cases will be different from other random N-mers in a given partition, e.g., primer sequence 516), the oligonucleotide anneals with the fragment 518, and is extended to create a complement 526 to at least a portion of fragment 518 which includes sequence 528, that comprises a duplicate of a portion of the sample nucleic acid sequence. Extension of the oligonucleotide 508b continues until it has replicated through the oligonucleotide portion 508 of fragment 518. As noted elsewhere herein, and as illustrated in panel D, the oligonucleotides may be configured to prompt a stop in the replication by the polymerase at a desired point, e.g., after replicating through sequences 516 and 514 of oligonucleotide 508 that is included within fragment 518. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 512 to prevent a non-uracil tolerant polymerase to cease replication of that region. As a result a fragment 526 is created that includes the full-length oligonucleotide 508b at one end, including the barcode sequence 512, the attachment sequence 510, the R1 primer region 514, and the random N-mer sequence 516b. At the other end of the sequence will be included the complement 516' to the random N-mer of the first oligonucleotide 508, as well as a complement to all or a portion of the R1 sequence, shown as sequence 514'. The R1 sequence 514 and its complement 514' are then able to hybridize together to form a partial hairpin structure 528. As will be appreciated because the random N-mers differ among different oligonucleotides, these sequences and their complements would not be expected to participate in hairpin formation, e.g., sequence 516', which is the complement to random N-mer 516, would not be expected to be complementary to random N-mer sequence 516b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 526.

Figure 6:
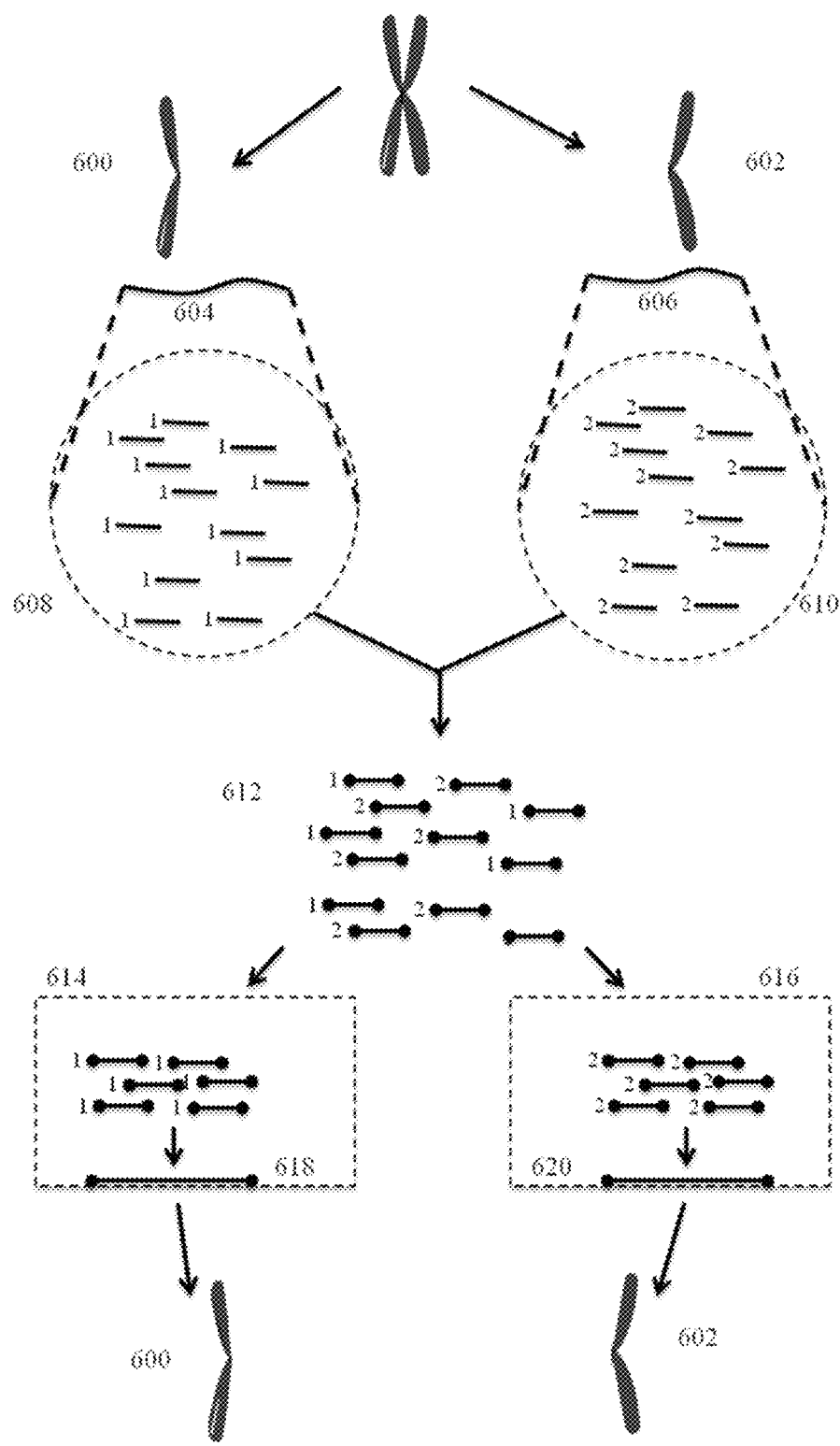
FIG. 6 provides a schematic illustration of the use of barcoding of chromosomal nucleic acid fragments in attributing sequence data to individual chromosomes.

All of the fragments from multiple different partitions may then be pooled for sequencing on high throughput sequencers as described herein. Because each fragment is coded as to its partition of origin, the sequence of that fragment may be attributed back to its origin based upon the presence of the barcode. This is schematically illustrated in FIG. 6. As shown in one example, a nucleic acid 604 originated from a first source 600 (e.g., individual chromosome, strand of nucleic acid, etc.) and a nucleic acid 606 derived from a different chromosome 602 or strand of nucleic acid are each partitioned along with their own sets of barcode oligonucleotides as described above.

Within each partition, each nucleic acid 604 and 606 is then processed to separately provide overlapping set of second fragments of the first fragment(s), e.g., second fragment sets 608 and 610. This processing also provides the second fragments with a barcode sequence that is the same for each of the second fragments derived from a particular first fragment. As shown, the barcode sequence for second fragment set 608 is denoted by "1" while the barcode sequence for fragment set 610 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 608 and 610, may then be pooled for sequencing using, for example, sequence by synthesis technologies available from Illumina or Ion Torrent division of Thermo Fisher, Inc. Once sequenced, the sequence reads 612 can be attributed to their respective fragment set, e.g., as shown in aggregated reads 614 and 616, at least in part based upon the included barcodes, and optionally, and preferably, in part based upon the sequence of the fragment itself. The attributed sequence reads for each fragment set are then assembled to provide the assembled sequence for each sample fragment, e.g., sequences 618 and 620, which in turn, may be further attributed back to their respective original chromosomes (600 and 602). Methods and systems for assembling genomic sequences are described in, for example, U.S. patent application Ser. No. 14/752,773, filed Jun. 26, 2015, the full disclosure of which is hereby incorporated by reference in its entirety.

III. Application of Methods and Systems to Targeted Sequencing

In one aspect of the systems and methods described herein are used to obtain sequence information from targeted regions of a genome.

By "targeted" regions of a genome (as well as any grammatical equivalents thereof) is meant a whole genome or any one or more regions of a genome identified as of interest and/or selected through one or more methods described herein. The targeted regions of the genome sequenced by methods and systems described herein include without limitation introns, exons, intergenic regions, or any combination thereof. In certain examples, the methods and systems described herein provide sequence information on whole exomes, portions of exomes, one or more selected genes (including selected panels of genes), one or more introns, and combinations of intronic and exonic sequences.

Targeted regions of the genome may also include certain portions or percentages of the genome rather than regions identified by sequence. In certain embodiments, targeted regions of the genome captured and analyzed in accordance with the methods described herein include portions of the genome located every 1, 2, 5, 10, 15, 20, 25, 50, 100, 200, 250, 500, 750, 1000, or 10000 kilobases of a genome. In further embodiments, targeted regions of the genome comprise 5%, 10%, 15%, 20%, 30%, 40%, 50%, 60%, 70%, 80%, 90%, 95% of the whole genome. In still further embodiments, the targeted regions comprise 1-10%, 5-20%, 10-30%, 15-40%, 20-50%, 25-60%, 30-70%, 35-80%, 40-90%, or 45-95% of the whole genome.

In general, targeted regions of a genome are captured for use in any sequencing methods known in the art and described herein. By "captured" as used herein is meant any method or system for enriching a population of nucleic acid and/or nucleic acid fragments such that the resultant population contains an increased percentage of the targeted regions of interest as compared to the genomic regions that are not of interest. In further embodiments, the enriched population contains at least 50%, 55%, 60%, 70%, 75%, 80%, 85%, 90%, 95%, 97%, 98%, 99%, or 100% nucleic acids/nucleic acid fragments comprising the targeted regions.

Capture methods generally include chip-based methods, in which targeted regions are captured through hybridization or other association with capture molecules on a surface, and solution based methods, in which oligonucleotide probes (baits), which are complementary to the targeted regions (or to regions near the targeted regions) are hybridized to genomic fragment libraries. The probes used in the capture methods disclosed herein are generally attached to capture molecules, such as biotin, which can be used to "pull down" the probes and the fragments to which they are hybridized— these pull down methods include any methods by which the baits hybridized to nucleic acids or nucleic acid fragments that contain the targeted regions of interest are separated from fragments that do not contain the regions of interest. In embodiments in which the probes are biotynilated, magnetic streptavidin beads are used to selectively pull-down and enrich baits with bound targeted regions.

In further aspects, a library of baits is used that covers all the targeted regions desired for further study. In the case of whole exome analysis, such a library of baits thus includes oligonucleotide probes that together cover the full exome. In certain embodiments, only portions of the exome are needed for further analysis. In such embodiments, the baits are designed to target that subset of the exome. This design can be accomplished using methods and algorithms known in the art and in general is based upon a reference sequence, such as the human genome.

In some examples, the targeted genomic regions processed and sequenced in accordance with the methods and systems described herein are full or partial exomes. These full or partial exomes can be captured for sequencing using any methods known in the art, including without limitation any of the Roche/NimbleGen exome protocols, including the NimbleGen 2.1M Human Exome array and the NimbleGen SeqCap EZ Exome Library, any of the Agilent SureSelect products, any Illumina exome capture products, including the TruSeq and Nextera Exome products, and any other products, methods, systems and protocols known in the art.

In further embodiments, when the targeted regions of interest comprise whole or portions of the exome, the baits used to capture those targeted regions may be designed to be complementary to those exonic sequences. In other embodiments, the baits are not complementary to the exonic sequences themselves but are instead complementary to sequences near the exonic sequence or to intronic sequences between two exons. Such designs are also referred to herein as "anchored exome capture" or "intronic baiting," by which, as discussed herein, is meant a process in which one or more portions of an exome are captured through the use of baits complementary to one or more intronic sequences near or adjacent to the one or more portions of the exome that are of interest. For example, as schematically illustrated in FIG. 2, a genomic sequence 201 comprises exonic regions 202 and 203. Those exonic regions can be captured by utilizing baits directed to one or more of the intronic sequences nearby (for example intronic region 204 and/or 205 to capture exonic region 202 and intronic region 206 for capture of exonic region 203). In other words, a population of fragments comprising exonic regions 202 or 203 would be captured through the use of baits complementary to intronic regions 204 and/or 205 and 206. In some embodiments, intronic baiting is used to bridge exons separated by long intronic regions by sparsely baiting longer introns. In such embodiments, the baits are not necessarily targeting intronic regions that are close to the exonic regions of interest, but the baits are instead designed to target regions separated by particular distances (or sets of distances) or are designed to tile across the intronic regions by a particular number of bases or combinations of numbers of bases. Such embodiments are described in further detail below.

In some embodiments, the intronic regions used for anchored exome capture/intronic baiting techniques of the invention are adjacent to the exonic region to be captured. In further embodiments, the intronic regions are separated from the exonic region to be captured by about 1-50, 2-45, 3-40, 4-35, 5-30, 6-25, 7-20, 8-15, 9-10, 2-20, 3-15, 4-10, 5-30, 10-40, 15-50, 20-75, 25-100 nucleotides. In still further embodiments, the intronic regions are separated from the exonic regions to be captured by about 5, 10, 20, 30, 40, 50, 60, 70, 80, 90, 100, 125, 150, 175, 200, 300, 400, or 500 nucleotides. In further embodiments, particularly for situations in which sparse baiting of intronic regions is of use (such as for phase variant detection or identification of linked exonic regions across large intronic distances) the intronic regions are separated from the exonic regions to be captured by distances on the orders of kilobases, e.g., 1-20, 2-18, 3-16, 4-14, 5-12, 6-10 kilobases. Since the original molecular context of the enriched population of oligonucleotides is retained, this sparse baiting of intronic regions allows for the linking of sequence information between exonic regions separated by long introns.

In further aspects, rather than designing the baits to target particular regions of the genome, a tiling approach is used. In such an approach, rather than targeting specific exonic or intronic regions, the baits are instead designed to be complementary to portions of the genome at particular ranges or distances. For example, the library of baits can be designed to hybridize to sequences located every 5 kilobases (kb) along the genome, such that applying this library of baits to a fragmented genomic sample will capture only a certain subset of the genome—i.e., those regions that are contained in fragments containing complementary sequences to the baits. As will be appreciated, the baits can be designed based on a reference sequence, such as a human genome reference sequence. In further embodiments, the tiled library of baits is designed to capture regions every 1, 2, 5, 10, 15, 20, 25, 50, 100, 200, 250, 500, 750, 1000, or 10000 kilobases of a genome. In some examples, this tiling method has the effect of sparsely capturing intronic regions, thus providing a way to link sequence information of exonic regions that are separated by long intronic regions, because the original molecular context of those exonic regions captured through sparse capture of intronic regions is retained.

In still further embodiments, the baits are designed to tile the genome in a random or combined manner—for example, a mixture of tiled libraries can be used where some of the libraries capture regions every 1 kb, whereas other libraries in the mixture capture regions every 100 kb. In still further embodiments, the tiled libraries are designed so that the baits target within a range of positions within the genome—for example, the baits may target regions of every 1-10, 2-5, 5-200, 10-175, 15-150, 20-125, 30-100, 40-75, 50-60 kb of the genome. In further examples, the tiled or other capture methods described herein will capture about 5%, 10%, 15%, 20%, 30%, 40%, 50%, 60%, 70%, 80%, 90%, 95% of the whole genome. As will be appreciated, such tiling methods of capture will capture both intronic and exonic regions of the genome for further analysis such as sequencing.

In yet further embodiments and in accordance with any of the methods described herein, the library of baits used in methods of the present invention is a product of informed design that fulfills one or more characteristics as further described herein. This informed design includes instances in which the library of baits is directed to informative single nucleotide polymorphisms (SNPs). As discussed above, the term "informative SNPs" as used herein refers to SNPs that are heterozygous. The library of baits in some examples is designed to contain a plurality of probes that are directed to regions of the genomic sample that contain informative SNPs. By "directed to" as used herein is meant that the probes contain sequences that are complementary to those regions of the genomic sequences. Informed bait design provides the ability to optimize targeted sequencing methods by allowing for targeted enrichment with full coverage while at the same time reducing the number of probes needed (and thus reducing costs and streamlining the work flow).

Figure 8:
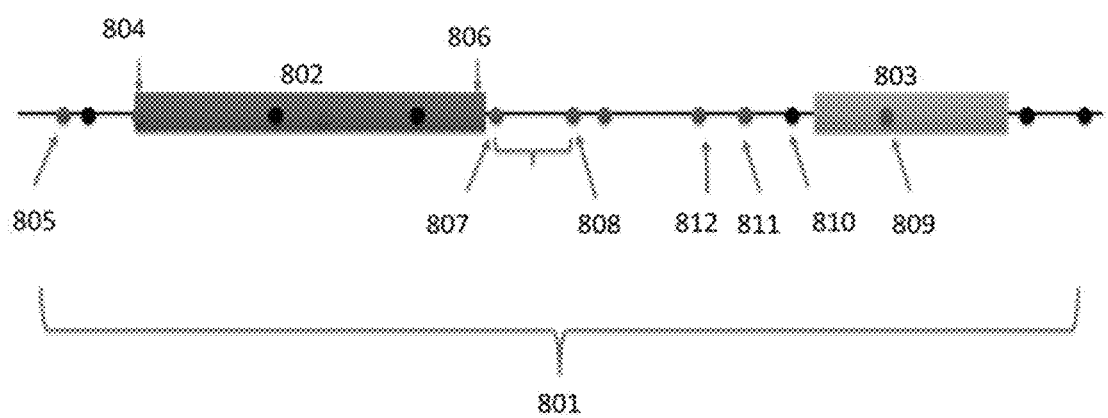
FIG. 8 illustrates a general embodiment of a method of the invention.

In general, for methods utilizing informed bait design, the libraries of baits are designed to include baits directed to particular sequences in targeted regions of the genome based on the presence or absence of informative SNPs in those regions and/or the location(s) of those informative SNPs. An exemplary illustration of general considerations for informed bait design is provided in FIG. 8. A region of the genome 801 can include exons (802 and 803). In some examples, an informative SNP 804 will be located at the boundary between the exon (802) and the adjacent intron. In such a situation, the bait library can be designed to include probes directed to one or more nucleotides (805) at a specified distance away from the boundary. In further examples in which there is no informative SNP at the boundary between the exon and the adjacent intron (806), the bait library can be designed to include probes directed to one or more positions in the intron near that boundary (807 and 808). Those positions will preferably include informative SNPs, but may also include other SNPs and/or other sequences as needed. In still further examples in which an exon 803 contains an informative SNP 809 in the interior of the exon but no informative SNPs at the boundaries, the bait library can be designed to include probes directed to several positions 810, 811, and 812 in the adjacent intron that include a mixture of informative and non-informative SNPs (as well as any other sequences as needed).

In some aspects, one or more input characteristics are used to design a probe bait library that is directed to shifting locations along the genome based on those input characteristics as well as map quality in various regions. This design is generally based on spacing between informative SNPs rather than on the locations of introns and exons. However, as will be appreciated, any of the descriptions provided herein related to bait design based on intron and exon locations can also be used in combination with the informed bait design methods based on informative SNPs. Input characteristics used in informed bait design include without limitation and in any combination locations of exons, introns, intergenic regions, informative SNPs, as well as regions of repeating sequences (such as GC-rich regions), centromeres, and sample nucleic acid lengths.

For ease of discussion, different characteristics of informed design probe libraries are described below in terms of different potential embodiments. As will be appreciated, any of the probe libraries discussed herein, whether using any of the informed design elements or any of the other types of design discussed above can be used singly or in any combination. The design elements utilized are selected based on the targeted genomic regions of interest as well as sample input and the quality of mapping for those regions of interest.

In some embodiments, probe bait libraries are designed to include probes directed to regions that have a high likelihood of containing informative SNPs in a given sample. Such targets may include individual bases (the informative SNPs themselves) or one or more bases that are proximal or adjacent to the informative SNPs. In still further embodiments, the targets for the probe baits may be directly adjacent to the informative SNPs or separated by distances from about 1-200, 10-190, 20-180, 30-170, 40-160, 50-150, 60-140, 70-130, 80-120, 90-100 bases from an informative SNP.

In further embodiments, the probe bait libraries include probes directed to regions of particular densities related to the average length of the nucleic acid molecules. For example, the probes can be designed to include probes at a density of target sequences that is x-fold more dense than the average length of the nucleic acid molecules/fragments to which the probes are hybridizing, where x can be without limitation 1, 5, 10, 20, 50, 75, 100, 125, 150, or 200. Increasing the density of the probe targets relative to the length of the nucleic acids increases the ability to link probes across loci on the same physical molecule. Such methods can also improve the probability that the linked regions will include informative SNPs, thus further improving the ability of the probe bait libraries to attach to targeted regions of the genome.

The density of the probe targets may also be increased in situations in which (at the population level) there is not a high probability of informative SNPs in a given region of interest. In such regions, tiling methods such as those described herein can be used to direct probes at periodic spacings along the region. In certain embodiments, the density of the spacing can be differentially based, such that the density of probe spacing in these regions lacking informative SNPs are at a 1, 2, 5, 10, 25, 50-fold shorter distance than probe spacing in regions containing informative SNPs.

In further embodiments, the probe bait library is designed to consider only informative SNP distribution within a gene (including exons and introns). This method of design is directed to capture a sufficient number of heterozygous SNPs at key locations to link/phase from one end of the gene to the other. Such a design method includes baits directed to sets of targets that combine exonic informative SNPs with one or more non-exonic SNPs such that the distance between informative SNPs in a gene is below the above described densities of spacing.

Such informed design methods allow detection of not only general targeted regions of the genome, but also allows the detection and phasing of genomic structural variations, such as translocations and gene fusions. By ensuring that any individual gene can be phased, it follows that the vast majority of gene fusion events can be detected and phased using the methods described herein.

In certain embodiments and in accordance with any of the above, the bait libraries are designed to target probes at distances of about 1 kb to about 2 Mb. In further embodiments, the distances are from about 1-50, 5-45, 10-40, 15-35, 20-30, 10-50 kb.

In further embodiments, the nucleic acid fragments being targeted by the probe baits are from about 2 kb to about 250 Mb. In still further embodiments, the fragments are from about 10-1000, 20-900, 30-800, 40-700, 50-600, 60-500, 70-400, 80-300, 90-200, 100-150, 50-500, 25-300 kb.

In some embodiments, the probe bait libraries are designed such that about 60-95% of the probes hybridize to sequences containing informative SNPs. In further embodiments, the probe bait libraries are designed such that about 65%-85%, 70%-80%, 60-90%, 80-90%, 90-95%, 95%-99% of the probes in the library of probes are designed to hybridize to informative SNPs. In still further embodiments, at least 65%, 75%, 85%, 90%, 91%, 92%, 93%, 94%, 95%, 96%, 97% of the probes in the library of probes are designed to hybridize to informative SNPs. As will be appreciated, for a probe to be designed to "hybridize to" an informative SNP means that such a probe hybridizes to a sequence region that includes that informative SNP.

In further embodiments, the probe bait libraries are designed to include a plurality of probes directed to informative SNPs that are located within both exons and introns in targeted portions of the genomic sample.

In still further embodiments, the libraries are designed such that a majority of the probes in the library hybridize to informative SNPs spaced apart by about 1-15, 5-10, 3-6 kb. In yet further embodiments, the majority of the probes in the library of probes are further designed to hybridize to informative SNPs spaced apart by about 1, 3, 5, 10, 20, 30, 50 kb.

In further embodiments, a plurality of probes within the library of probes are designed such that for targeted portions of the genomic samples in which there are no informative SNPs within 5-300, 10-50, 20-100, 30-150, or 40-200 kb of boundaries between exons and introns, the plurality of probes is designed to hybridize at an informative SNP within an intron from those boundaries.

In further embodiments, a plurality of probes within the library of probes are designed such that for targeted portions of the genomic samples in which there is a first informative SNP within an exon and that first informative SNP is located 5-300, 10-50, 20-100, 30-150, or 40-200 kb from a boundary with an adjacent intron and a second informative SNP within the adjacent intron and that second informative SNP is located 10-50 kb from the boundary, the plurality of probes is designed to hybridize to a region of the genomic sample between the first and second informative SNPs;

In further embodiments, a plurality of probes within the library of probes are designed such that for targeted portions of the genomic samples comprising no informative SNPs for at least 5-300, 10-50, 20-100, 30-150, or 40-200 kb, the plurality of probes is designed to hybridize every 0.5, 1, 3, or 5 kb to those targeted portions of the genomic samples. In further embodiments, the plurality of probes is designed to hybridize every 0.1, 0.5, 1, 1.5, 3, 5, 10, 15, 20, 30, 35, 40, 45, 50 kb along those targeted portions of the genomic samples.

In further embodiments, a plurality of probes within the library of probes are designed such that for targeted portions of the genomic samples in which there are no informative SNPs within 5-300, 10-50, 20-100, 30-150, or 40-200 kb of boundaries between exons and introns, the plurality of probes are designed to hybridize to the next closest informative SNP to the exon-intron boundaries.

In further embodiments, the library of probes comprises probes designed to hybridize to regions of the genomic sample that flank exons at a density that provides linkage information across barcodes.

In still further embodiments, the range of coverage represented by the library of probes is inversely proportional to the distribution of lengths of the individual nucleic acid fragment molecules of the genomic sample in the discrete partitions, such that methods containing a higher proportion of longer individual nucleic acid fragment molecules use libraries of probes with smaller ranges of coverage.

In still further embodiments, the library of probes is optimized for coverage of the targeted portions of the genomic sample. In yet further embodiments, the density of coverage may be lower for regions of high map quality, particularly for those regions containing informative SNPs, and the density may further be higher for regions of low map quality to ensure that linkage information is provided across targeted regions.

In yet further embodiments, the library of probes has features informed by characteristics of the one or more targeted portions of a genomic sample, such that for targeted portions with high map quality, the library of probes comprises probes that hybridize to informative SNPs within 1 kb-1 Mb of boundaries of exons and introns. The library of probes may in such situations further include probes that hybridize to informative SNPs within 10-500, 20-450, 30-400, 40-350, 50-300, 60-250, 70-200, 80-150, 90-100 kb of boundaries of exons and introns.

In yet further embodiments, the library of probes has features informed by characteristics of the one or more targeted portions of a genomic sample, such that for targeted portions in which the distribution of lengths of the barcoded fragments has a high proportion of fragments longer than about 100, 150, 200, 250 kb, the library of probes comprise probes that hybridize to informative SNPs separated by at least 50 kb. The library of probes may in such situations further include probes that hybridize to informative SNPs separated by at least 5, 10, 15, 20, 25, 30, 35, 40, 45, 50, 75, 100, 125, 150, 175, 200 kb.

In yet further embodiments, the library of probes has features informed by characteristics of the one or more targeted portions of a genomic sample, such that for targeted portions with low map quality, the library of probes comprises probes that hybridize to informative SNPs within 1 kb of exon-intron boundaries. The library of probes may in such situations further include probes that hybridize to informative SNPs within 2, 5, 10, 15, 20, 25, 30, 35, 40, 45, 50, 75, 100, 125, 150, 175, 200 kb of exon-intron boundaries. In such situations, the library will further include probes that hybridize and probes that hybridize to informative SNPs within exons, within introns, or both.

In yet further embodiments, the library of probes has features informed by characteristics of the one or more targeted portions of a genomic sample, such that for targeted portions comprising intergenic regions, the library of probes comprises probes that hybridize to informative SNPs spaced apart at distances of at least 1, 2, 5, 10, 15, 20, 25, 30, 35, 40, 45, 50, 75, 100 kb.

The baits used in the capture methods described herein can be of any size or structure that is useful for enriching a population of fragments for fragments containing targeted regions of the genome. As discussed above, generally the baits of use in the present invention comprise oligonucleotide probes that are attached to a capture molecule, such as biotin. The oligonucleotide probes may be complementary to sequences within a targeted region of interest, or they may be complementary to regions outside of the targeted region but close enough to that targeted region that both the "anchoring" region and the targeted region are within the same fragment, such that the bait is able to pull down the targeted region by hybridizing to that nearby region (such as a flanking intron).

The capture molecule attached to the bait may be any capture molecule that can be used for isolating the bait and its hybridization partner from other fragments in a population. In general, the baits used herein are attached to biotin, and then solid supports comprising streptavidin (including without limitation magnetic streptavidin beads) can be used to capture the baits and the fragments to which they are hybridized. Other capture molecule pairs may include without limitation biotin/neutravidin, antigen/antibody, or complementary oligonucleotide sequences.

In further embodiments, the oligonucleotide probe portion of the baits can be of any length suitable for hybridizing to targeted regions or to regions near targeted regions. In some embodiments, the oligonucleotide probe portion of the baits used in accordance with the methods described herein—i.e., the portion that hybridizes to the targeted region of the genome or to a region near the targeted region—generally has a length from about 10 to about 150 nucleotides in length (e.g., 35 nucleotides, 50 nucleotides, 100 nucleotides) and is chosen to specifically hybridize to a target sequence of interest. In further embodiments, the oligonucleotide probe portion comprises a length of about 5-10, 10-50, 20-100, 30-90, 40-80, 50-70, nucleotides in length. As will be appreciated, any of the oligonucleotide probe portions described herein may comprise RNA, DNA, non-natural nucleotides such as PNAs, LNAs, and so on, or any combinations thereof.

An advantage of the methods and systems described herein is that the targeted regions that are captured are processed prior to capture in such a way that even after the steps of capturing the targeted regions and conducting sequencing analyses, the original molecular context of those targeted regions is retained. The ability to attribute specific targeted regions to their original molecular context (which can include the original chromosome or chromosomal region from which they are derived and/or the location of particular targeted regions in relation to each other within the full genome) provides a way to obtain sequence information from regions of the genome that are otherwise poorly mapped or have poor coverage using traditional sequencing techniques.

For example, some genes possess long introns that are too long to span using generally available sequencing techniques, particularly using short-read technologies. Short-read technologies are often preferable sequencing technologies, because they possess superior accuracy as compared to long-read technologies. However, generally used short-read technologies are unable to span across long regions of the genome, and thus information may not be obtainable using these conventional technologies in regions of the genome that are difficult to characterize due to structural characteristics such as long lengths of tandem repeating sequences, high GC content, and exons containing long introns. In the methods and systems described herein, however, the molecular context of targeted regions is retained, generally through the tagging procedure illustrated in FIG. 1 and described in further detail herein. As such, links can be made across extended regions of the genome. For example, as schematically illustrated in FIG. 2B, nucleic acid molecule 207 contains two exons (shaded bars) with a long intronic region (208). In the methods described herein, the individual nucleic acid molecule 207 is distributed into its own discrete partition 211 and then fragmented such that different fragments contain different portions of the exons and the intron. Because each of those fragments is tagged such that any sequence information obtained from the fragments is then attributable to the discrete partition in which it was generated, each fragment is thus also attributable to the individual nucleic acid molecule 207 from which it was derived.

In general, and as is described in further detail herein, after fragmentation and tagging, fragments from different partitions are combined together. Targeted capture methods can then be used to enrich the population of fragments that undergoes further analysis, such as sequencing, with fragments containing the targeted region of interest. In the example illustrated in FIG. 2B, the baits used will enrich the population of fragments to capture only those containing a portion of the exons, but regions outside of the exon and intron (such as 209 and 210) would not be captured. Thus, the final population of fragments that undergoes sequencing will be enriched for the fragments containing the portions of the exons, even if those exons are separated by a long intronic region. Short read, high accuracy sequencing technologies can then be used to identify the sequences of this enriched population of fragments, and because each of the fragments is tagged and thus attributable to its original molecular context, i.e., its original individual nucleic acid molecule, the short read sequences can be pieced together to provide information about the relationship between the exons. In some embodiments, the baits used to capture fragments containing all or part of one or more exons are complementary to one or more portions of the one or more exons themselves. In other embodiments, the baits are complementary to one or more portions of the intervening introns or to sequences adjacent to or near the exon on either the 3' or 5' side of the exon regions (such baits are also referred to herein as "intronic baits"). In further embodiments, the baits used to capture the fragments containing all or part of the exon include baits complementary to the exon itself and intronic baits.

The ability to retain the molecular context of the targeted regions captured for sequencing also provides the advantage of allowing for sequencing across poorly characterized regions of the genome. As will be appreciated, a significant percentage (at least 5-10% according to, for example Altemose et al., PLOS Computational Biology, May 15, 2014, Vol. 10, Issue 5) of the human genome remains unassembled, unmapped, and poorly characterized. The reference assembly generally annotates these missing regions as multi-megabase heterochromatic gaps, found primarily near centromeres and on the short arms of the acrocentric chromosomes. This missing fraction of the genome includes structural features that remain resistant to accurate characterization using generally used sequencing technologies. By providing the ability to link information across extended regions of the genome, the methods described herein provide a way to allow for sequencing across these poorly characterized regions.

In some examples, sample preparation methods, including methods of fragmenting, amplifying, partitioning, and otherwise processing genomic DNA, can lead to biases or lower coverage of certain regions of a genome. Such biases or lowered coverage can be compensated for in the methods and systems disclosed herein by altering the concentration of baits used to capture targeted regions of the genome. For example, in some situations it is known that certain regions of the genome will have low coverage after the fragment library is processed, such as regions containing high GC content or other structural variations that lead to bias toward certain areas of the genome over others. In such situations, the library of baits can be altered to increase the concentration of baits directed to those regions of low coverage—in other words, the population of baits used may be "spiked" to ensure that a sufficient number of fragments containing targeted regions of the genome in those low coverage areas are obtained in the final population of fragments to be sequenced. Such spiking of baits may be conducted through design of custom libraries in some embodiments. In further embodiments, the spiking of baits can be conducted in commercially available whole exome kits, such that a custom library of baits directed toward the lower coverage regions are added to off-the-shelf exome capture kits.

An advantage of the methods and systems described herein is that the targeted regions that are captured are processed prior to capture in such a way that even after the steps of capturing the targeted regions and conducting sequencing analyses, the original molecular context of those targeted regions is retained. As is discussed in further detail herein, the ability to attribute specific targeted regions to their original molecular context (which can include the original chromosome or chromosomal region from which they are derived and/or the location of particular targeted regions in relation to each other within the full genome) provides a way to obtain sequence information from regions of the genome that are otherwise poorly mapped or have poor coverage using traditional sequencing techniques.

For example, some genes possess long introns that are too long to span using generally available sequencing techniques, particularly using short-read technologies that possess superior accuracy as compared to long-read technologies. In the methods and systems described herein, however, the molecular context of targeted regions is retained, generally through the tagging procedure illustrated in FIG. 1 and described in further detail herein. As such, links can be made across extended regions of the genome. For example, as schematically illustrated in FIG. 2B, nucleic acid molecule 207 contains exons (shaded bars) interrupted by a long intronic region. Generally used sequencing technologies would be unable to span the distance across the intron to provide information on the relationship between the two exons. In the methods described herein, the individual nucleic acid molecule 207 is distributed into its own discrete partition 209 and then fragmented such that different fragments contain different portions of the exons and the intron. Because each of those fragments is tagged such that any sequence information obtained from the fragments is then attributable to the discrete partition in which it was generated, each fragment is thus also attributable to the individual nucleic acid molecule 207 from which it was derived. In general, and as is described in further detail herein, after fragmentation and tagging, fragments from different partitions are combined together. Targeted capture methods can then be used to enrich the population of fragments that undergoes further analysis, such as sequencing, with fragments containing the targeted region of interest. In the example illustrated in FIG. 2B, the baits used will enrich the population of fragments to capture only those containing a portion of one of exons, but regions outside of the exons (such as 209 and 210) would not be captured. Thus, the final population of fragments that undergoes sequencing will be enriched for the fragments containing the exons of interest. Short read, high accuracy sequencing technologies can then be used to identify the sequences of this enriched population of fragments, and because each of the fragments is tagged and thus attributable to its original molecular context, i.e., its original individual nucleic acid molecule, the short read sequences can be pieced together to span across the length of the intervening intron (which can in some examples be on the order of 1, 2, 5, 10 or more kilobases in length) to provide linked sequence information on the two exons.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. By providing longer range individual molecular context, the methods and systems of the invention also provide much longer inferred molecular context. Sequence context, as described herein can include lower resolution context, e.g., from mapping the short sequence reads to the individual longer molecules or contigs of linked molecules, as well as the higher resolution sequence context, e.g., from long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

IV. Samples

As will be appreciated, the methods and systems discussed herein can be used to obtain targeted sequence information from any type of genomic material. Such genomic material may be obtained from a sample taken from a patient. Exemplary samples and types of genomic material of use in the methods and systems discussed herein include without limitation polynucleotides, nucleic acids, oligonucleotides, circulating cell-free nucleic acid, circulating tumor cell (CTC), nucleic acid fragments, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like. In summary, the samples that are used may vary depending on the particular processing needs.

Any substance that comprises nucleic acid may be the source of a sample. The substance may be a fluid, e.g., a biological fluid. A fluidic substance may include, but not limited to, blood, cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. The substance may be solid, for example, a biological tissue. The substance may comprise normal healthy tissues, diseased tissues, or a mix of healthy and diseased tissues. In some cases, the substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The substance may be associated with various types of organs. Non-limiting examples of organs may include brain, liver, lung, kidney, prostate, ovary, spleen, lymph node (including tonsil), thyroid, pancreas, heart, skeletal muscle, intestine, larynx, esophagus, stomach, or combinations thereof. In some cases, the substance may comprise a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, the substance may comprise contents of a cell, such as, for example, the contents of a single cell or the contents of multiple cells. Methods and systems for analyzing individual cells are provided in, e.g., U.S. patent application Ser. No. 14/752,641, filed Jun. 26, 2015, the full disclosure of which is hereby incorporated by reference in its entirety, particularly all teachings related to analyzing nucleic acids from individual cells.

Samples may be obtained from various subjects. A subject may be a living subject or a dead subject. Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. In some case, the subject may be a normal healthy pregnant woman. In some cases, the subject may be a pregnant woman who is at a risking of carrying a baby with certain birth defect.

A sample may be obtained from a subject by any means known in the art. For example, a sample may be obtained from a subject through accessing the circulatory system (e.g., intravenously or intra-arterially via a syringe or other apparatus), collecting a secreted biological sample (e.g., saliva, sputum urine, feces, etc.), surgically (e.g., biopsy) acquiring a biological sample (e.g., intra-operative samples, post-surgical samples, etc.), swabbing (e.g., buccal swab, oropharyngeal swab), or pipetting.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Whole Exome Capture and Sequencing: NA12878

Genomic DNA from the NA12878 human cell line was subjected to size based separation of fragments using a Blue Pippin DNA sizing system to recover fragments that were greater than or equal to approximately 10 kb in length. The size selected sample nucleic acids were then copartitioned with barcode beads in aqueous droplets within a fluorinated oil continuous phase using a microfluidic partitioning system (See, e.g., U.S. patent application Ser. No. 14/682,952, filed Apr. 9, 2015, and incorporated herein by reference in its entirety for all purposes), where the aqueous droplets also included the dNTPs, thermostable DNA polymerase and other reagents for carrying out amplification within the droplets, as well as DTT for releasing the barcode oligonucleotides from the beads. This was repeated both for 1 ng of total input DNA and 2 ng of total input DNA. The barcode beads were obtained as a subset of a stock library that represented barcode diversity of over 700,000 different barcode sequences. The barcode containing oligonucleotides included additional sequence components and had the general structure:

Bead-P5-BC-R1-Nmer

Where P5 and R1 refer to the Illumina attachment and Read1 primer sequences, respectively, BC denotes the barcode portion of the oligonucleotide, and Nmer denotes a random 10 base N-mer priming sequence used to prime the template nucleic acids. See, e.g., U.S. patent application Ser. No. 14/316,383, filed Jun. 26, 2014, the full disclosure of which is hereby incorporated herein by reference in its entirety for all purposes.

Following bead dissolution, the droplets were thermocycled to allow for primer extension of the barcode oligos against the template of the sample nucleic acids within each droplet. This resulted in amplified copy fragments of the sample nucleic acids that included the barcode sequence representative of the originating partition, in addition to the other included sequences set forth above.

After barcode labeling of the copy fragments, the emulsion of droplets including the amplified copy fragments was broken and the additional sequencer required components, e.g., read2 primer sequence and P7 attachment sequence, were added to the copy fragments through an additional amplification step, which attached these sequences to the other end of the copy fragments. The barcoded DNA was then subjected to hybrid capture using an Agilent SureSelect Exome capture kit.

The table below provides targeting statistics for the NA 12878 genome:

| Sample | Median Insert Size | % Fragments on Target | % Bases on Target |
| --- | --- | --- | --- |
| Version 1.A | 258 | 81% | 51% |
| Version 1.B | 224 | 81% | 55% |
| Version 1.C | 165 | 81% | 63% |

The three different versions listed above represent three different shear lengths for the barcoded fragments before the second adapter attachment step.

Example 2: Whole Exome Capture and Sequencing: NA19701 and NA19661

Genomic DNA from the NA19701 and NA19661 cell lines was prepared according to the methods described above in Example 1. Data, including phasing data, from those two cells lines is provided in the table below:

| | NA19661 | NA19701 |
| --- | --- | --- |
| N50_phase_block | 29,535 | 83,953 |
| N90_phase_block | 8,595 | 25,684 |
| mean_phase_block | 5,968 | 21,128 |
| median_phase_block | 0 | 76.5 |
| longest_phase_block | 209,323 | 504,140 |
| fract_genes_phased | 0.719 | 0.641 |
| fract_genes_completely_phased | 0.679 | 0.776 |
| fract_snps_phased | 0.669 | 0.632 |
| fract_snps_barcode | 0.644 | 0.607 |
| fract_snps_barcode_both_alleles | 0.328 | 0.351 |
| prob_snp_correct_in_gene | 0.906 | 0.927 |

-continued

|  | NA19661 | NA19701 |
|---|---|---|
| prob_snp_phased_in_gene | 0.807 | 0.888 |
| snp_short_switch_error | 0.013 | 0.013 |
| snp_long_switch_error | 0.012 | 0.013 |

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method of obtaining sequence information from one or more targeted portions of a genomic sample, the method comprising:
    (a) providing a plurality of fragments from the genomic sample in discrete partitions, wherein each of the fragments further comprises a barcode, and wherein at least first and second fragments within 10 kb of each other in a contiguous sequence of the genomic sample comprise a common barcode, and wherein the discrete partitions are flowable within fluid streams;
    (b) applying a library of probes directed to the one or more targeted portions of the genomic sample to the plurality of fragments;
    (c) conducting a first sequencing reaction to identify sequences of the plurality of fragments that hybridized to the library of probes, thereby obtaining sequence information from the one or more targeted portions of the genomic sample;
    (d) conducting a second sequencing reaction to identify sequences of fragments from the discrete partitions that did not hybridize to the library of probes.

2. The method of claim 1, wherein about 80%-99% of the probes in the library of probes are designed to hybridize to informative SNPs.

3. The method of claim 1, wherein about 65%-85% of the probes in the library of probes are designed to hybridize to informative SNPs.

4. The method of claim 1, wherein at least 65% of the probes in the library of probes are designed to hybridize to informative SNPs.

5. The method of claim 1, wherein at least 75% of the probes in the library of probes are designed to hybridize to informative SNPs.

6. The method of claim 1, wherein the one or more targeted portions comprise informative SNPs, and the informative SNPs are located within both exons and introns in the targeted portions of the genomic sample.

7. The method of claim 1, wherein the majority of the probes in the library of probes are designed to hybridize to informative SNPs spaced apart by about 1 kilobase (kb) to about 15 kb.

8. The method of claim 1, wherein a plurality of probes within the library of probes are further designed to meet one or more of the following conditions in any combination:
    (i) for targeted portions of the genomic samples in which there are no informative SNPs within 10-50 kb of boundaries between exons and introns, the plurality of probes is designed to hybridize at an informative SNP within an intron from those boundaries;
    (ii) for targeted portions of the genomic samples in which there is a first informative SNP within an exon and that first informative SNP is located 10-50 kb from a boundary with an adjacent intron and a second informative SNP within the adjacent intron and that second informative SNP is located 10-50 kb from the boundary, the plurality of probes is designed to hybridize to a region of the genomic sample between the first and second informative SNPs;
    (iii) for targeted portions of the genomic samples comprising no informative SNPs for at least 10-50 kb, the plurality of probes is designed to hybridize every 0.5, 1, 3, or 5 kb to those targeted portions of the genomic samples;
    (iv) for targeted portions of the genomic samples in which there are no informative SNPs within 10-50 kb of boundaries between exons and introns, the plurality of probes are designed to hybridize to the next closest informative SNP to the exon-intron boundaries.

9. The method of claim 1, wherein the library of probes comprises probes designed to hybridize to regions of the genomic sample that flank exons at a density that provides linkage information across barcodes.

10. The method of claim 1, wherein a range of coverage represented by the library of probes is inversely proportional to the distribution of lengths of the individual nucleic acid fragment molecules of the genomic sample in the discrete partitions, such that a higher proportion of longer individual nucleic acid fragment molecules results in use of libraries of probes with smaller ranges of coverage.

11. The method of claim 1, wherein the sequence information obtained in step (c) comprises information on one or more members of the group consisting of: gene fusions, copy number variations, insertions, and deletions.

12. The method of claim 1, wherein the library of probes is designed to hybridize to sequences at defined distances along the genome.

13. The method of claim 1, wherein the library of probes is designed to hybridize to sequences at a random mixture of distances along the genome.

14. The method of claim 1, wherein the library of probes is designed to hybridize to sequences at one or more of 20, 50, 100, 200, 250, or 500 kb along the genome.

15. The method of claim 1, wherein the library of probes is designed to hybridize to both intronic and exonic regions of the genome.

16. The method of claim 1, wherein the method further comprises step (e) determining linkage of the two or more targeted portions of the genomic sample based upon common barcode sequences.

17. The method of claim 1, wherein the discrete partitions comprise droplets of aqueous fluid within a non-aqueous continuous phase.

18. The method of claim 1, wherein the barcode is selected from a plurality of barcodes comprising at least 100,000 different sequences.

* * * * *